(12) United States Patent
Zdeblick

(10) Patent No.: US 7,935,056 B2
(45) Date of Patent: May 3, 2011

(54) INTRAVASCULARLY IMPLANTABLE INTEGRATED CIRCUITS

(75) Inventor: Mark J. Zdeblick, Portola Valley, CA (US)

(73) Assignee: Proteus Biomedical, Inc., Redwood City, CA (US)

( * ) Notice: Subject to any disclaimer, the term of this patent is extended or adjusted under 35 U.S.C. 154(b) by 1069 days.

(21) Appl. No.: 11/731,247

(22) Filed: Mar. 29, 2007

(65) Prior Publication Data

US 2007/0185537 A1   Aug. 9, 2007

Related U.S. Application Data

(63) Continuation of application No. 11/219,305, filed on Sep. 1, 2005, now Pat. No. 7,214,189.

(60) Provisional application No. 60/707,995, filed on Aug. 12, 2005, provisional application No. 60/679,625, filed on May 9, 2005, provisional application No. 60/638,928, filed on Dec. 23, 2004, provisional application No. 60/607,280, filed on Sep. 2, 2004.

(51) Int. Cl.
   *A61N 1/08*   (2006.01)
(52) U.S. Cl. ........................................... 600/300; 607/2
(58) Field of Classification Search .............. 607/9, 115, 607/2; 600/300
   See application file for complete search history.

(56) References Cited

U.S. PATENT DOCUMENTS

| | | | |
|---|---|---|---|
| 4,397,314 A | 8/1983 | Vaguine | |
| 4,399,820 A | 8/1983 | Wirtzfeld et al. | |
| 4,603,705 A | 8/1986 | Speicher et al. | |
| 4,628,934 A | 12/1986 | Pohndorf et al. | |
| 4,776,334 A | 10/1988 | Prionas | |
| 4,815,472 A | 3/1989 | Wise et al. | |
| 4,877,032 A | 10/1989 | Heinze et al. | |
| 4,878,898 A | 11/1989 | Griffin et al. | |
| 4,881,410 A | 11/1989 | Wise et al. | |

(Continued)

FOREIGN PATENT DOCUMENTS

WO   WO 02/065894 A2   8/2002

(Continued)

OTHER PUBLICATIONS

Auricchio et al.; "The Pacing Therapies for Congestive Heart Failure (PATGH-CHF) Study: Rationale, Design and Endpoints of a Prospective Randomized Multicenter Study;" *Am J Cardiol*; 83:130D-135D. (1999).

(Continued)

*Primary Examiner* — Eric D. Bertram
(74) *Attorney, Agent, or Firm* — Bret E. Field; Bozicevic Field & Francis LLP

(57) ABSTRACT

Techniques for controlling one or more modular circuits ("satellites") that are intended for placement in a subject's body. The one or more satellites are controlled by sending signals over a bus that includes first and second conduction paths. Also coupled to the bus in system embodiments is a device such as a pacemaker that provides power and includes control circuitry. Each satellite includes satellite circuitry and one or more effectors that interact with the tissue. The satellite circuitry is coupled to the bus, and thus interfaces the controller to the one or more effectors, which may function as actuators, sensors, or both. The effectors may be electrodes that are used to introduce analog electrical signals (e.g., one or more pacing pulses) into the tissue in the local areas where the electrodes are positioned (e.g., heart muscles) or to sense analog signals (e.g., a propagating depolarization signal) within the tissue.

12 Claims, 17 Drawing Sheets

U.S. PATENT DOCUMENTS

| | | |
|---|---|---|
| 4,902,273 A | 2/1990 | Choy et al. |
| 5,004,275 A | 4/1991 | Miller |
| 5,035,246 A | 7/1991 | Heuvelmans et al. |
| 5,072,737 A | 12/1991 | Goulding |
| 5,113,868 A | 5/1992 | Wise et al. |
| 5,156,154 A | 10/1992 | Valenta, Jr. et al. |
| 5,213,098 A | 5/1993 | Bennett et al. |
| 5,391,199 A | 2/1995 | Ben-Haim |
| 5,411,532 A | 5/1995 | Mortazavi |
| 5,411,537 A | 5/1995 | Munshi et al. |
| 5,417,717 A | 5/1995 | Salo et al. |
| 5,419,767 A | 5/1995 | Eggers et al. |
| 5,423,323 A | 6/1995 | Orth |
| 5,509,411 A | 4/1996 | Littmann et al. |
| 5,535,752 A | 7/1996 | Halperin |
| 5,544,656 A | 8/1996 | Pitsillades et al. |
| 5,549,650 A | 8/1996 | Bornzin et al. |
| 5,579,764 A | 12/1996 | Goldreyer |
| 5,591,142 A | 1/1997 | Van Erp |
| 5,593,430 A | 1/1997 | Renger |
| 5,662,587 A | 9/1997 | Grundfest et al. |
| 5,683,429 A | 11/1997 | Mehra |
| 5,720,768 A | 2/1998 | Verboven-Nelissen |
| 5,743,267 A | 4/1998 | Nikolic et al. |
| 5,788,647 A | 8/1998 | Eggers |
| 5,800,465 A | 9/1998 | Thompson et al. |
| 5,810,735 A | 9/1998 | Halperin et al. |
| 5,814,089 A | 9/1998 | Stokes et al. |
| 5,902,234 A | 5/1999 | Webb |
| 5,902,248 A | 5/1999 | Miller et al. |
| 5,913,814 A | 6/1999 | Zantos |
| 5,924,997 A | 7/1999 | Campbell |
| 5,935,084 A | 8/1999 | Southworth |
| 5,999,848 A * | 12/1999 | Gord et al. ............ 607/2 |
| 6,015,386 A | 1/2000 | Kensey et al. |
| 6,024,704 A | 2/2000 | Meador et al. |
| 6,033,398 A | 3/2000 | Farley et al. |
| 6,038,480 A | 3/2000 | Hrdlicka et al. |
| 6,078,830 A | 6/2000 | Levin et al. |
| 6,081,748 A | 6/2000 | Struble et al. |
| 6,155,267 A | 12/2000 | Nelson |
| 6,165,135 A | 12/2000 | Neff |
| 6,171,252 B1 | 1/2001 | Roberts |
| 6,206,835 B1 | 3/2001 | Spillman, Jr. et al. |
| 6,206,874 B1 | 3/2001 | Ubby et al. |
| 6,234,973 B1 | 5/2001 | Meador et al. |
| 6,264,606 B1 | 7/2001 | Ekwall et al. |
| 6,277,078 B1 | 8/2001 | Porat et al. |
| 6,287,256 B1 | 9/2001 | Park et al. |
| 6,299,582 B1 | 10/2001 | Brockway et al. |
| 6,301,500 B1 | 10/2001 | Van Herk et al. |
| 6,309,350 B1 | 10/2001 | Van Tassel et al. |
| 6,309,385 B1 | 10/2001 | Simpson |
| 6,328,699 B1 | 12/2001 | Eigler et al. |
| 6,360,123 B1 | 3/2002 | Kimchi |
| 6,363,279 B1 | 3/2002 | Ben-Haim et al. |
| 6,370,431 B1 | 4/2002 | Stoop et al. |
| 6,418,348 B1 | 7/2002 | Witte |
| 6,438,408 B1 | 8/2002 | Mulligan et al. |
| 6,466,820 B1 | 10/2002 | Juran et al. |
| 6,473,653 B1 | 10/2002 | Schallhorn et al. |
| 6,477,395 B2 | 11/2002 | Schuman et al. |
| 6,477,417 B1 | 11/2002 | Levine |
| 6,496,730 B1 | 12/2002 | Kleckner et al. |
| 6,580,946 B2 | 6/2003 | Struble |
| 6,611,714 B1 | 8/2003 | Mo |
| 6,628,989 B1 | 9/2003 | Penner et al. |
| 6,666,826 B2 | 12/2003 | Salo et al. |
| 2001/0002924 A1 | 6/2001 | Tajima |
| 2001/0047138 A1 | 11/2001 | Kokate et al. |
| 2001/0053882 A1 | 12/2001 | Haddock et al. |
| 2002/0026183 A1 | 2/2002 | Simpson |
| 2002/0045921 A1 | 4/2002 | Wolinsky et al. |
| 2002/0077568 A1 | 6/2002 | Haddock |
| 2002/0077673 A1 | 6/2002 | Penner et al. |
| 2002/0095196 A1 | 7/2002 | Linberg |
| 2002/0111560 A1 | 8/2002 | Kokate et al. |
| 2002/0120186 A1 | 8/2002 | Keimel |
| 2002/0151816 A1 | 10/2002 | Rich et al. |
| 2002/0156417 A1 | 10/2002 | Rich et al. |
| 2002/0161307 A1 | 10/2002 | Yu et al. |
| 2002/0169445 A1 | 11/2002 | Jain et al. |
| 2003/0153952 A1 | 8/2003 | Auricchio et al. |
| 2004/0193021 A1 | 9/2004 | Zdeblick et al. |
| 2004/0220637 A1 | 11/2004 | Zdeblick et al. |
| 2004/0254483 A1 | 12/2004 | Zdeblick et al. |

FOREIGN PATENT DOCUMENTS

| | | |
|---|---|---|
| WO | WO 02/065894 A3 | 8/2002 |
| WO | WO 2004/052182 A2 | 6/2004 |
| WO | WO 2004/052182 A3 | 6/2004 |
| WO | WO 2004/066814 A2 | 8/2004 |
| WO | WO 2004/066814 A3 | 8/2004 |
| WO | WO 2004/066817 A2 | 8/2004 |
| WO | WO 2004/066817 A3 | 8/2004 |
| WO | WO 2004/067081 A2 | 8/2004 |
| WO | WO 2004/067081 A3 | 8/2004 |

OTHER PUBLICATIONS

Borky, J.M. and Wise, K.D.; "Integrated Signal Conditioning for Silicon Pressure Sensors;" *IEEE Transactions on Electron Devices*, ED-26(12):1906-1910 (1979).

Kovacs, "Technology Development for a Chronic Neutral Interface;" A dissertation, Stanford University (Aug. 1990), pp. 9, 225-234, 257, 276.

Receveur, et al., "Latterally Moving Bi-Stable MEMS DC-Switch for Biomedical Applications;" Medtronic Bakken Research Center, The Netherlands, pp. 854-856 (2004).

* cited by examiner

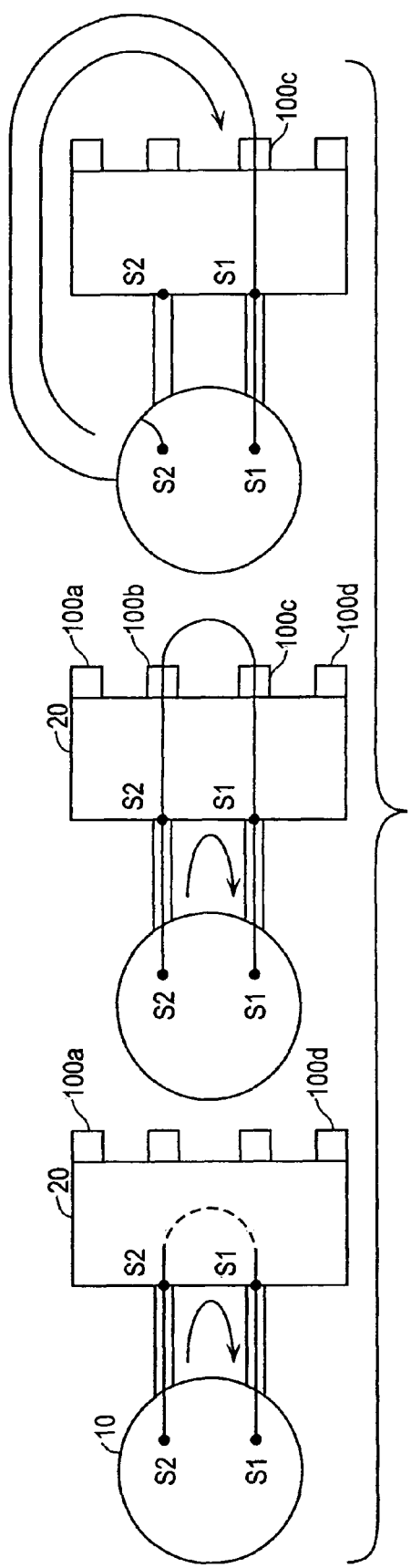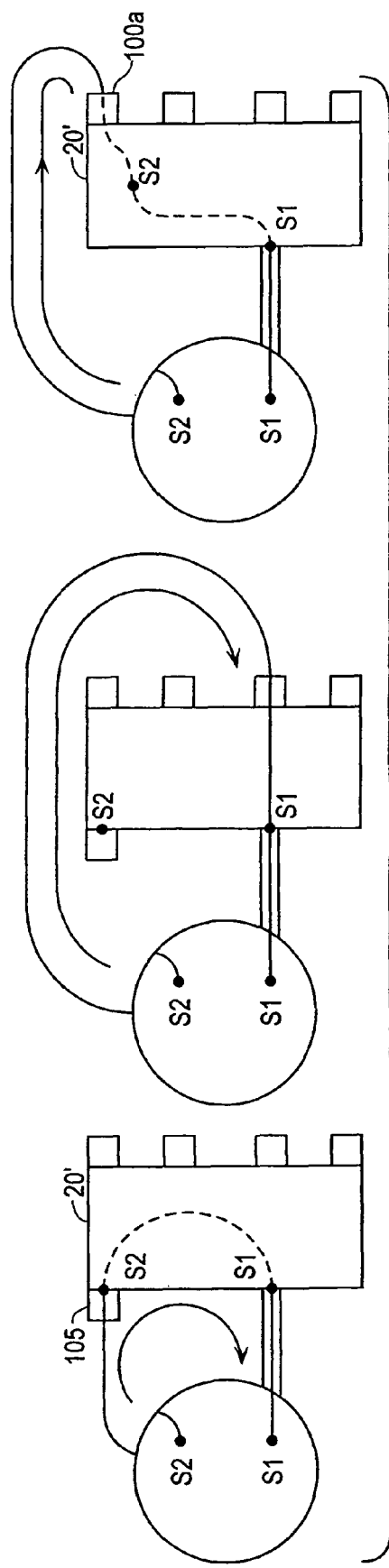
FIG. 16A
FIG. 16B

INTRAVASCULARLY IMPLANTABLE INTEGRATED CIRCUITS

CROSS REFERENCE TO RELATED APPLICATIONS

This application is a continuation application of U.S. Application Ser. No. 11/219,305 filed Sep. 1, 2005; which application claims priority under 35 U.S.C. §119 from the following provisional applications:

U.S. Provisional Patent Application No. 60/707,995, filed Aug. 12, 2005, titled "Methods and Apparatus for Tissue Activation and Monitoring" by inventor Mark Zdeblick;

U.S. Provisional Patent Application No. 60/679,625, filed May 9, 2005, titled "De Minimus Control Circuit for Cardiac Pacing and Signal Collection" by inventor Mark Zdeblick;

U.S. Provisional Patent Application No. 60/638,928, filed Dec. 23, 2004, titled "Methods and Systems for Programming and Controlling a Cardiac Pacing Device" by inventor Mark Zdeblick; and U.S. Provisional Patent Application No. 60/607,280, filed Sep. 2, 2004, titled "One Wire Medical Monitoring and Treating Devices" by inventor Mark Zdeblick.

The entire disclosures (including any attachments or appendices) of the above patent applications and those of the following commonly owned patent applications are hereby incorporated by reference for all purposes:

U.S. patent application Ser. No. 10/764,127, filed Jan. 23, 2004, titled "Methods and Systems for Measuring Cardiac Parameters" by inventors Mark Zdeblick and Joseph M. Ruggio (published Dec. 16, 2004 as No. 20040254483);

U.S. patent application Ser. No. 10/764,429, filed Jan. 23, 2004, titled "Method and Apparatus for Enhancing Cardiac Pacing" by inventors Mark Zdeblick and Joseph M. Ruggio (published Nov. 4, 2004 as No. 20040220637);

U.S. patent application Ser. No. 10/764,125, filed Jan. 23, 2004, titled "Method and System for remote Hemodynamic Monitoring" by inventors Mark Zdeblick and Joseph M. Ruggio (published Oct. 28, 2004 as No. 20040215049); and U.S. patent application Ser. No. 10/734,490, filed Dec. 11, 2003, titled "Method and System for Monitoring and Treating Hemodynamic Parameters" by inventors Mark Zdeblick and George M. Savage (published Sep. 30, 2004 as No. 20040193021).

BACKGROUND OF THE INVENTION

The present invention relates to administering electrical signals to local areas of living tissue and monitoring conditions in such tissue. In particular, the present invention relates to a low-power modular circuit for controlling one or more electrodes that can be used to administer or monitor such electrical signals.

Electrodes for administering electrical signals or for monitoring electrical signals at specific locations in living tissue, such as the heart, are important tools used in many medical treatment or diagnosis. U.S. Pat. No. 6,473,653, entitled "Selective Activation of Electrodes within an Implantable Lead," to Schallhom et al., filed on Mar. 2, 2000, discloses an implantable multi-electrode lead adapted to allow selective activation of the included electrodes to electrically excite the tissue in the vicinities of the activated electrodes. U.S. Pat. No. 5,593,430, entitled "Bus System for Interconnecting an Implantable Medical Device with a Plurality of Sensors," to Renger, filed on Jan. 27, 1995, discloses a two-conductor bus system for connecting physiologic sensors to a pacemaker. The two-conductor bus provides power to the sensors, and the sensors' output signals are modulated on the two wires.

SUMMARY OF THE INVENTION

In broad terms, the invention provides methods and apparatus for controlling one or more modular circuits ("satellites" or "satellite units") that are intended for placement in a subject's (typically, but not necessarily, human) body. The one or more satellites are controlled by sending signals over a bus that includes first and second conduction paths (usually referred to as bus conduction paths). Also coupled to the bus in system embodiments is a device such as a pacemaker that provides power and includes control circuitry. For convenience, this device will be referred to as the central controller, although as will be seen below, it may itself be a distributed system.

Each satellite includes satellite circuitry and one or more devices that interact with the tissue. The satellite circuitry includes at least one active device, and is typically an integrated circuit ("satellite chip"). The satellite circuitry is coupled to the bus, and thus interfaces the central controller to the one or more devices. Typically, the devices that interact with the body ("interacting devices" or "effectors") may function as actuators (sometimes referred to as activators), sensors, or both. For example, these effectors may be electrodes that are used to introduce analog electrical signals (e.g., one or more pacing pulses) into the living tissue in the local areas where the electrodes are positioned (e.g., heart muscles) or to sense analog signals (e.g., a propagating depolarization signal) within the living tissue.

The bus is typically used to carry analog and digital signals, and, at various times during operation, may be used to do one or more of the following: transmit digital information from the central controller to the satellites, send configuration information from the central controller to the satellites to configure one or multiple effectors associated with selected satellites, provide a power supply to operate the digital logic circuits within the satellite chip, transmit activation pulses from the central controller to the satellites, transmit analog signals from the satellites to the central controller, and transmit digital signals (e.g., signals confirming the configuration) from the satellites to the central controller.

Some embodiments include one or more individually addressable satellites, and the central controller is able to configure or otherwise control one or more selected satellites. In such embodiments, the bus may be used to transmit address information from the central controller to the satellites, send configuration information from the central controller to the satellites to configure one or multiple effectors associated with selected satellites.

Different embodiments are characterized by different implementations of the first and second bus conduction paths, or portions thereof. In some embodiments, a bus conduction path is said to be insulated from the subject's body. Such a conduction path includes a discrete conductive element (e.g., a wire; namely a dedicated conductor) that is distinct from the subject's body and an insulating material separating the conductive element from the subject's body. In this context, "insulated" should be taken to include the possibility that there may be small leakage currents, but that efforts have been made to insulate the conduction path from the subject's tissue.

In other embodiments, a bus conduction path is not insulated from the subject's body. Such a conduction path may include a discrete conductive element that is in contact with the subject's body, or may be defined by the subject's body so that the conduction is through the subject's tissue and/or body fluids. In some embodiments, a conduction path (referred to as a hybrid conduction path) includes a portion that is insulated from the subject's body and a portion that is not insulated from the subject's body. The portion of the conduction path that is not insulated can include a discrete conductive element in contact with the body or can be defined by a portion of the subject's body, or can include both.

In some embodiments, at least one of the bus conduction paths is associated with a carrier such as a pacing lead, and the satellites are placed along the carrier. The satellite-bearing carrier is intended to be implanted or otherwise inserted into tissue (e.g., the heart) so as to interact with the tissue.

As a result, a system based on embodiments of the present invention has significantly increased flexibility and accuracy, whether used for activation or sensing. For example, in one embodiment, one carrier accommodates eight satellites, each controlling four electrodes. Such a configuration allows the system to select, and activate or sense with various combinations of the 32 electrodes with a desired sequence.

Embodiments of the present invention include satellite chips that consume very little power. Thus, a satellite chip in some embodiments can remain in a configured state for a long period of time without being recharged. In one embodiment, the satellite chip need only be recharged after a time interval exceeding 30 minutes and draws only a current in the order of a few picoamps. To save power, the satellite chip stores the satellite and electrode address and configuration information in registers, and shuts off power for idle portions of the digital circuits. As a result of this low power capability, the satellites of the present invention may be easily incorporated into commercial pacing systems.

The term "wire" is sometimes used for one of the bus conduction paths, and in some embodiments, the satellite chip contact terminal or terminals are bonded to a metal wire. However, the term "wire" should be interpreted broadly to include non-metallic solid conducting or semiconducting materials, and also channels filled with conductive polymers, fluids, gels, pastes, and the like. In some instances, the satellite chip terminal contacts will contact a conductive fluid or gel, which may itself contact another conductive solid material. Further, while metal electrodes are contemplated, other conductive materials (e.g., silicides) could be used.

In one set of embodiments, referred to as two-wire embodiments, the first and second bus conduction paths are insulated from each other and from the subject's body, and both are typically associated with the carrier. In another set of embodiments, referred to as one-wire embodiments, one of the conduction paths is insulated from the subject's body, but the other is defined in part or whole by the subject's body. In a third set of embodiments, both conduction paths are defined in whole or in part by the subject's body.

In one aspect of the invention a method for configuring one or more effectors situated within a satellite unit that resides in a subject's body includes: receiving signals over a bus; and based on the signals received over the bus, deriving a relatively stable DC voltage for supplying the circuitry, recovering clock and digital data, interpreting bit sequences in the digital data to extract configuration information, and using the bit sequences to store configuration information for the one or more desired effectors.

In another aspect of the invention, a medical apparatus includes: a carrier unit configured for insertion into a subject's body; a bus having at least one conduction path, at least a part of which is insulated from the subject's body when the carrier is inserted into the subject's body, and a plurality of satellite units located along the carrier and connected to the bus. Each satellite unit includes one or more effectors that interact with the subject's body when the carrier is inserted into the subject's body, and satellite circuitry that is coupled to the bus. The satellite circuitry is structured to receive power over the bus, receive a bit sequence over the bus, and store information based on the bit sequence.

In another aspect of the invention, a method for controlling one or more satellite units which reside along a carrier located in a subject's body includes: supplying power to one or more of the satellite units over a bus, transmitting a bit sequence over the bus, and storing information in at least one satellite unit based on the bit sequence. The bus includes first and second conduction paths with at least the first conduction path being insulated from the subject's body when the carrier is located within the subject's body.

In another aspect of the invention, a method for configuring one or more effectors situated within a satellite unit that resides along a carrier located in a subject's body includes: receiving signals over a bus; and, based on the signals received over the bus, deriving a relatively stable DC voltage for supplying the circuitry, recovering clock and digital data, interpreting bit sequences in the digital data to extract address information, and at least for cases where the address information matches stored address information, using the bit sequences to configure one or more desired effectors to be coupled to the first or the second conduction paths of the bus.

In another aspect of the invention, an integrated circuit for use to configure electrodes in an implanted lead includes: a first terminal; a second terminal; and circuitry coupled to the first and second terminals wherein, during a first time interval, during which digital configuration signals are provided from the controller on the first terminal, the circuitry selectively configures selected ones of the electrodes to the first terminal, and wherein, during a second time interval, the controller administers electrical signals through the configured electrodes by way of the first terminal.

In another aspect of the invention, a medical apparatus for interacting with a body includes: a controller-power source with at least a first electrode (e.g., the outside conductive surface of the housing) contacting the body; a satellite unit for placement within the body, the satellite unit including satellite circuitry connected to at least a second electrode, the second electrode being in electrical contact with the body; and a single conductor between the controller-power source and the satellite unit, wherein data and power current flow from the controller-power source through the single conductor to said satellite unit, through the second electrode, through the body, through the first electrode, and to the controller-power source.

A further understanding of the nature and advantages of the present invention may be realized by reference to the remaining portions of the specification and the drawings.

BRIEF DESCRIPTION OF THE DRAWINGS

FIG. 16A is a schematic representation of programming and pacing with a two-wire embodiment of the invention;

FIG. 16B is a schematic representation of programming and pacing with a two-wire embodiment of the invention;

DESCRIPTION OF SPECIFIC EMBODIMENTS

Introduction

Figure 1:
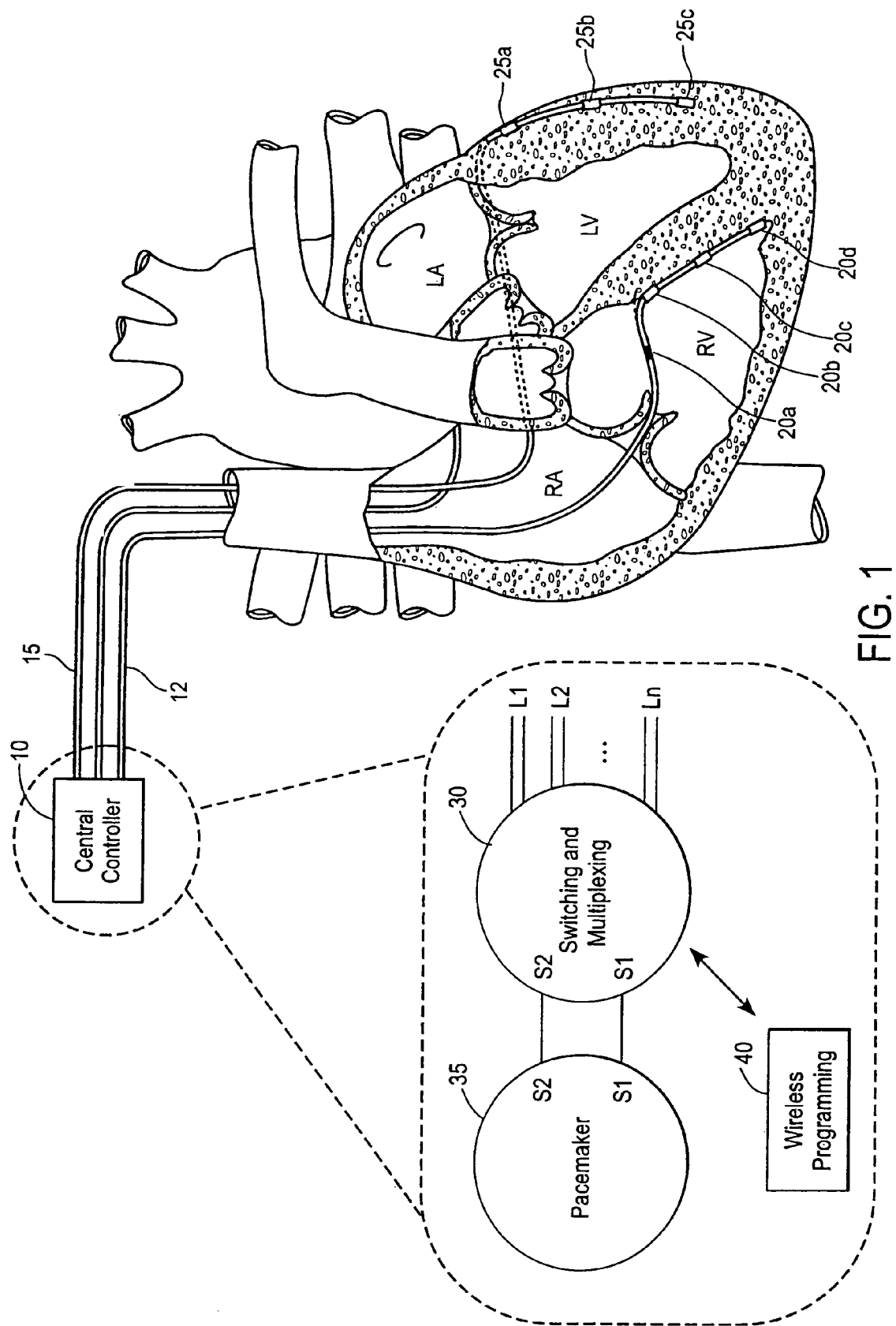
FIG. 1 is a schematic of an exemplary cardiac pacing and signal detection system.

The following description is presented to enable any person skilled in the art to make and use the invention, and is provided in the context of a particular application and its requirements. Various modifications to the disclosed embodiments will be readily apparent to those skilled in the art, and unless stated otherwise, the embodiments described should be considered exemplary.

In broad terms, the invention provides embodiments where one or more individually addressable modular circuits ("satellites" or "satellite units") are placed along a bus that includes at least one conductor associated with a carrier such as a pacing lead. The bus provides first and second conduction paths. In some embodiments ("two-wire embodiments"), as will be described below, both conduction paths are insulated from the subject's body. In other embodiments ("one-wire embodiments"), only one of the conduction paths is insulated from the subject's body while the other conduction path is provided by the conductive fluids in the subject's body.

In either case, the satellite-bearing carrier is intended to be implanted or otherwise inserted into tissue (e.g., the heart) so as to interact with the tissue. Each satellite includes satellite circuitry and one or more devices ("effectors") that interact with the tissue. In many of the specific embodiments, these effectors are electrodes, and for a cardiac application, they are used for pacing or sensing or both.

In the present application, terms such as "detecting" and "sensing" are used broadly. For example, consider where the satellite is configured to use a pair of its electrodes, which are in contact with the tissue, to make a measurement or determine when a specific condition is met (e.g., to detect a voltage change that signifies a depolarization signal).

In one set of embodiments, the satellite is configured to couple one or more desired electrodes to the bus so the central controller can sense the analog voltage that appears across the electrodes. The central controller performs those operations required to determine, based on the analog signal, if and when the condition has occurred, for example by determining that the voltage has exceeded a threshold (or met some other set of conditions) during the interval that the satellite has its electrodes coupled to the bus. In another set of embodiments, not specifically described, the satellite could include additional circuitry so that the satellite, in addition to experiencing the voltages, could determine when the analog voltage across its electrodes is such as to imply that the condition has been met, and could report such a determination to the central controller using the bus.

In both these sets of embodiments, the satellite can be considered to have detected the condition, although the central controller performs portions of the detection in the first set of embodiments. The second-mentioned set of embodiments require more functionality on the part of the satellite, for example, the ability to convert analog voltages to digital signals, and to transmit digital signals.

Although the strict definition of electric current considers the direction of current flow to be the direction in which positive charges flow, it is not intended in the present application to limit the direction that way. In other words, unless the context requires otherwise, a statement that current flows from one point to another does not imply a particular direction in which positive charges flow.

In the most comprehensive system operation, the satellites are inserted in a subject's body, and communicate with a central controller. However, subsystems have commercial and medical viability. For example, components for pacing may be implanted during an initial surgery, but not activated until needed, perhaps years later. When the subject is already undergoing heart surgery, implanting some of the components at that time tends to be much less invasive than implanting them later, especially after scar tissue arising from the surgery has formed. Even if the subject is not in need of pacing, the components may be activated for monitoring purposes, and later activated for pacing purposes if and when a need is found. Indeed, it may be advantageous to implant a two-dimensional mesh of satellites at the time of the surgery, even if none of the satellites are to be activated until later.

Location of Satellites for Cardiac Pacing or Signal Detection

FIG. 1 is a high level schematic of a cardiac pacing and signal detection system in which a number of satellite units (or satellites) are disposed on one or more pacing leads and communicate with a pacing and detection controller 10, typically referred to as the central controller. Central controller 10 provides extra-cardiac communication and control elements for the overall system of FIG. 1, and may include, for example, a pacing can of a pacemaker, typically implanted under a subject's skin away from the heart. In the specific configuration illustrated, there are three pacing leads, including a right ventricular lead 12 and a left ventricular lead 15.

Right ventricular lead 12 emerges from the central controller, and travels from the subcutaneous location of the central controller into the subject's body (e.g., preferably, a subclavian venous access), and through the superior vena cava into the right atrium. From the right atrium, right ventricular lead 12 is threaded through the tricuspid valve to a location along the walls of the right ventricle. The distal portion of right ventricular lead 12 is preferably located along the intra-ventricular septum, terminating with fixation in the right ventricular apex. Right ventricular lead 12 is shown as having satellites 20a, 20b, 20c, and 20d. In one optional configuration, satellite 20a includes a pressure sensor in the right ventricle.

Similarly, left ventricular lead 15 emerges from central controller 10, following substantially the same route as right ventricular lead 12 (e.g., through the subclavian venous access and the superior vena cava into the right atrium). In the right atrium, left ventricular lead 15 is threaded through the coronary sinus around the posterior wall of the heart in a cardiac vein draining into the coronary sinus. Left ventricular lead 15 is provided laterally along the walls of the left ventricle, which is a likely position to be advantageous for bi-ventricular pacing. Left ventricular lead 15 is shown as having satellites 25a, 25b, and 25c.

The number of satellites shown is but one example. In some embodiments, there may be more; in others, fewer. The particular implementation described below allows a large number of individually addressable satellites. A typical embodiment may provide four electrodes per satellite and eight satellites per lead. A signal multiplexing arrangement, according to embodiments of the present invention, facilitates including active devices (e.g., pressure sensor 20a) to a lead for pacing and signal collection purposes (e.g., right ventricular lead 12). As mentioned above and described below in detail, the electrodes controlled by the satellites may be used for pacing, and may also be used to detect analog signals, such as local analog cardiac depolarization signals.

Central Controller Overview

Central controller 10 is shown in an enlarged detail to be a distributed system, where multiplexing and switching capabilities are provided by a switching circuit 30 that augments a pacemaker 35 (commonly referred to as a pacemaker "can"), which may be any conventional pacemaker. The switching circuit acts as an interface between the pacemaker and a plurality of leads, designated L1 . . . Ln. Right and left ventricular leads 12 and 15 are examples of such leads, which are configured for placement within the heart in an arrangement and by procedures well known by those skilled in the art. The arrangement described above with respect to leads 12 and 15 is representative.

Switching circuit 30 may be housed within a can similar to that of pacemaker 35, which housing is configured for implantation in the subject adjacent to pacemaker 30. Switching circuit 30 is electrically coupled to pacemaker 30 via a pair of signal lines, which are referenced herein as S1 and S2, wherein S1 represents ground and S2 is a voltage supply. These lines may be configured at the pacemaker end in the form of a connector which can be plugged into standard pacemaker lead plug receptors.

Central controller 10 performs a number of functions, which will be outlined here. The precise division of labor between switching circuit 30 and pacemaker 35 can be a matter of design choice. To the extent that it is desired to implement embodiments of the present invention, the pacemaker can be considered to provide a power supply and the ability to generate pacing pulses of desired voltage and duration. For purposes of this discussion, switching circuit 30 will be described as providing the additional functionality. This is not critical, and indeed the pacemaker and the switching circuit can be implemented within a single housing.

In short, switching circuit 30 multiplexes the pacemaker signals among the various leads, although some signals may go to multiple leads. The switching circuit also sends signals to, and receives signals from, the satellites on the bus. At various times, the switching circuit may be used to transmit address information from the central controller to the satellites, send configuration information from the central controller to the satellites to configure one or multiple electrodes associated with selected satellites, provide power to operate the digital logic circuits within the satellite chip, transmit activation pulses from the pacemaker to the satellites, receive analog signals from the satellites, and receive digital signals (e.g., signals confirming the configuration) from the satellites.

Additionally, switching circuit 30 provides a communication link to external devices, such as a programmer 40, which can remotely-control and program the switching circuit with operating or functional parameters, certain parameters of which can then be communicated to pacemaker 35 by the switching circuit. While any mode of telemetry may be used to transfer data between switching circuit 30 and programmer 40, one suitable mechanism for use with implantable devices is electromagnetic coils, where one coil is provided in switching circuit 30 and another is provided in programmer 40. By placing the programmer in close proximity to the subject's chest in the vicinity of the implanted switching can, telemetric communication can be established.

Information transmitted between switching circuit 30 and programmer 40 is in the form of AC signals which are demodulated to extract a bit stream representing the digital information to be communicated. The signal(s) transmitted by programmer 40 and received by switching circuit 30 provides a series of commands for setting the system operating parameters. Such operating or functional parameters may include, but are not limited to, assignment of the electrode states, the pulse width, amplitude, polarity, duty cycle and duration of a pacing signal, the number of pulses per heart cycle, and the timing of the pulses delivered by the various active electrodes.

The AC signals sent from the programmer to the switching circuit can also provide a system operating current which can be used to power up the circuit components. To this end, the switching circuit can be provided with a rectifier bridge and a capacitor. In typical situations, the switching circuit gets its power from pacemaker 35, but could be provided with a separate battery if desired.

In addition to downloading information from a programming device, the switching circuit may also be configured to upload information such as sensing data collected and stored within a memory element of the switching circuit. Such sensing data may include, but is not limited to, blood pressure, blood volume, blood flow velocity, blood oxygen concentration, blood carbon dioxide concentration, wall stress, wall thickness, force, electric charge, electric current and electric conductivity.

The switching circuit may also be capable of storing and transmitting data such as cardiac performance parameters, which are calculated by it or the pacemaker from the sensed data. Such cardiac performance parameters may include, but are not limited to, ejection fraction, cardiac output, cardiac index, stroke volume, stroke volume index, pressure reserve, volume reserve, cardiac reserve, cardiac reserve index, stroke reserve index, myocardial work, myocardial work index, myocardial reserves myocardial reserve index, stroke work, stroke work index, stroke work reserve, stroke work reserve index, systolic ejection period, stroke power, stroke power reserve, stroke power reserve index, myocardial power, myocardial power index, myocardial power reserve, myocardial power reserve index, myocardial power requirement, ejection contractility, cardiac efficiency, cardiac amplification, valvular gradient, valvular gradient reserve, valvular area, valvular area reserve, valvular regurgitation, valvular regurgitation reserve, a pattern of electrical emission by the heart, and a ratio of carbon dioxide to oxygen within the blood.

Switching circuit 30 may also function as part of a satellite power management system. As will be described in greater detail below, each satellite has a capacitor that stores sufficient charge to power certain parts of the satellite circuitry (e.g., latches storing satellite configuration information) when power is not being provided over the bus. While leakage currents may be extremely low, and normal signaling and pacing may provide enough power to keep the capacitor charged, switching circuit may be configured to periodically supply a sufficiently high voltage pulse for a few microseconds, possibly from 10 to 20 microseconds, to recharge all the satellite capacitors. Additionally, switching circuit 30 can be programmed to periodically, e.g., once daily, refresh the then current satellite configuration that had been stored memory. In case of a power glitch which disrupts the electrode status, switching circuit 30 can reset the electrode capacitors to the last configuration stored in memory.

Another function which may be performed by switching circuit 30 is that of transmitting analog signals from the satellites to pacemaker 35. For example, where the pacemaker is attempting to sample voltages at a plurality of locations within the heart in order to generate a map of the heart's electrical potentials, switching circuit 30 enables this by providing high-speed switching between the electrodes selected for the voltage sampling. More specifically, over a very short time period, on the order of milliseconds, the electrical potential at a selected electrode is sampled, information regarding the analog voltage is sent to pacemaker 35, and the sequence is repeated for another selected electrode. The faster the switching, the more accurate the "snap shot" of potentials is at various locations about the heart, and thus, the more accurate the electrical potential map.

In some embodiments, the information regarding the analog voltage is the analog signal itself. That is, the measured potentials are provided as analog signals which are carried from the satellite electrodes to pacemaker 35 by way of switching circuit 30 where the signal from one electrode is provided on line S1 and the signal from another electrode is provided on line S2. An amplifier or voltage comparator circuit within pacemaker 35 may then compare the two analog voltages signals. Based on this comparison, pacemaker 35 will reconfigure the pacing parameters as necessary. Alternatively, each satellite chip could include an analog-to-digital converter that digitizes the analog voltage signal prior to sending it to switching circuit 30. It is believed that providing this additional functionality in the satellites would require larger satellite chips, would be more power consumptive, and would be slower since the time necessary for the charges on the capacitors in the satellites to settle and become balanced would be far greater. Thus, this approach is not preferred.

Still yet, switching circuit 30 may function as an analog-to-digital and digital-to-analog conversion system. A sensing protocol, either programmed within switching circuit 30 or otherwise transmitted by an external program by programmer 40, in the form of digital signals is converted to an AC signal by switching circuit 30. These analog signals include current signals which drive sensing electrodes or other types of sensors, e.g., transducers, to enable them to measure physiological, chemical and mechanical signals, e.g., conductance signals, within the subject's body. The measured signals, also in analog form, are then converted to digital signals by switching circuit 30 and stored in memory, used to calculate other parameters by the switching circuit or transmitted to pacemaker 35 and/or programmer 40 for further processing.

A multiple electrode lead allows for greater flexibility in lead placement as at least one of the multiple electrodes will be optimally positioned to pace the heart. Determining which of a lead's electrodes is best positioned to obtain or provide an accurate signal to and form the heart may be determined experimentally by controlled pacing of the heart and measuring the resulting threshold voltage of each electrode, wherein the electrode with the lowest threshold voltage is the most optimally positioned electrode for that satellite unit. Additionally, the electrode facing away from a nearby nerve may be preferred. For example, stimulation of the phrenic nerve can cause hiccups.

Once the electrode on each satellite unit with the lowest threshold or least sensitive to phrenic nerve stimulation is established, then the various satellite units may be selected one at a time or in combinations to determine which satellite unit(s) with its best electrode configuration produces the best hemodynamic response. This latter optimization may be performed with feedback from an external device such as an ultrasound system, or with one of the other feedback systems referenced in the above published applications.

System Architecture and Satellite Overview

Figure 2:
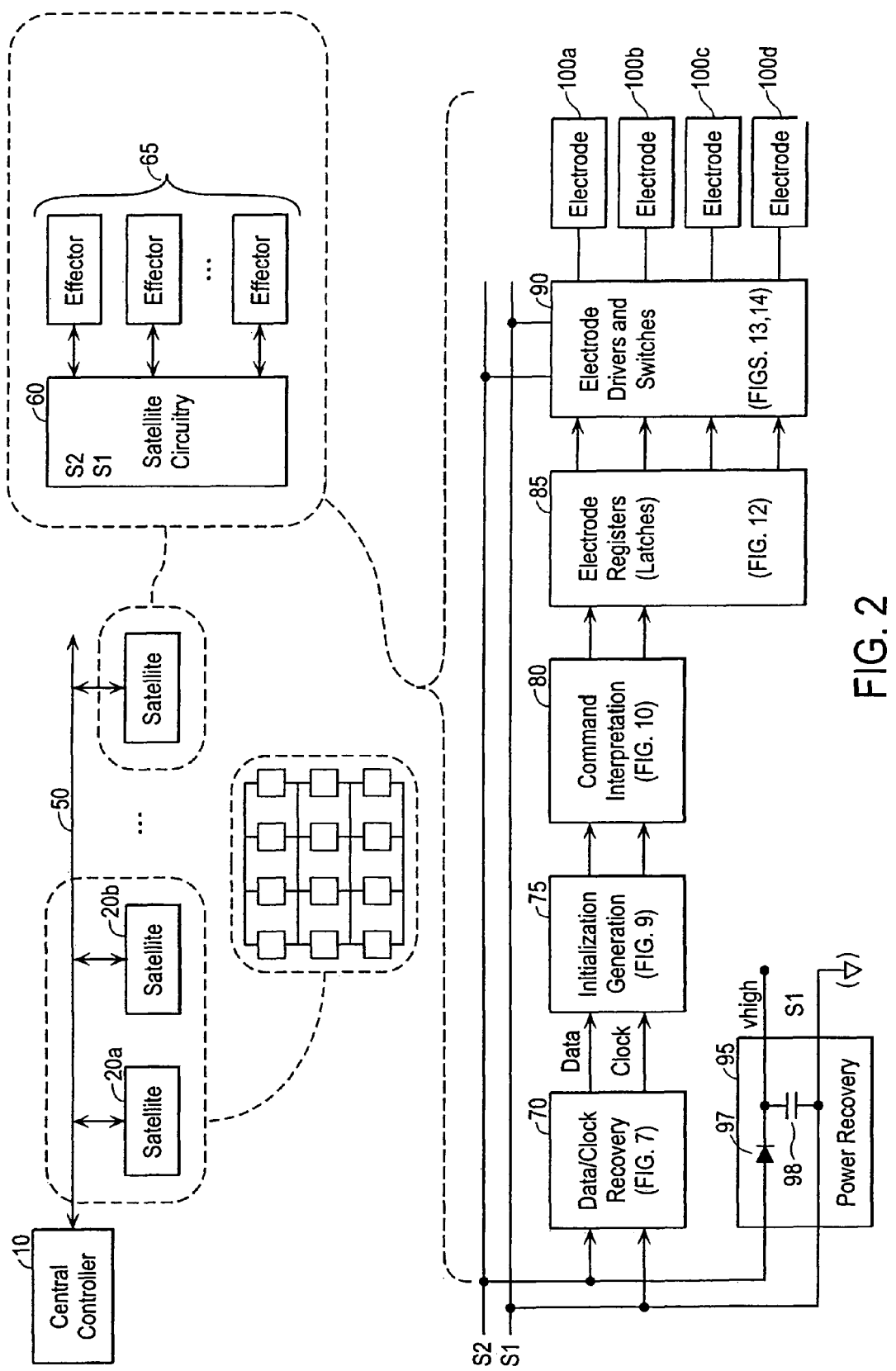
FIG. 2 is a high level block diagram of the communication between the central controller and a number of satellites, and also shows an exemplary satellite architecture.

FIG. 2 is a high level block diagram of the communication between central controller 10 and a number of satellites, designated 20a, 20b, . . . as suggesting these to be the satellites on right ventricular lead 12. Successively enlarged first- and second-level detail views show an exemplary satellite architecture. This figure shows the bus and satellites corresponding to a single lead, it being understood that similar view could be presented for other leads. As mentioned above, switching circuit 30 can multiplex and switch between leads.

The figure shows central controller communicating with the satellites over a bus 50, which is seen to have first and second conduction paths S1 and S2. As seen in the first-level detail view, the satellite includes satellite circuitry 60, typically an integrated circuit ("satellite chip") and a number of effectors 65 that interact with the tissue in which the satellites are implanted or otherwise inserted. Effectors 65 may function as actuators, sensors, or both. In many embodiments, the effectors are electrodes, and in much of the discussion that follows, effectors 65 will often be referred to as electrodes. It should be kept in mind, however, that they can be other types of actuators or sensors.

The satellite chip is shown as having two terminals S1 and S2, corresponding to the bus conduction paths. In a particular implementation, S1 is ground and S2 varies depending on the particular operation being performed, but a maximum DC voltage of 5 volts is typical. Also, while the figure shows bus conduction paths S1 and S2 as if they are wires, conduction path S2 is provided by the subject's body in the one-wire embodiments.

The second-level detail view shows the basic elements of the satellite chip in a representative embodiment. These basic elements include a data and clock recovery (DCR) circuit 70, an initialization generation circuit 75, a command interpretation circuit 80, electrode registers or latches 85 for storing electrode configuration information, an electrode driver and switch circuit 90, and a power recovery circuit 95. Power recovery circuit 95 includes a diode 97 (implemented as a diode-connected NMOS transistor in an exemplary implementation) and a capacitor 98 that stores sufficient charge to maintain certain portions of the satellite circuitry (e.g., stored configuration information) for significant periods of time when the satellite is not deriving power from the bus. The voltage on capacitor 98 is designated "vhigh."

In the second-level detail view, effectors 65 of the first-level detail-views are shown specifically as four electrodes 100a, 100b, 100c, 100d. As noted above, the invention is not limited to the effectors being electrodes, and further the invention is not limited to a specific number of effectors associated with a given satellite. Indeed, in some embodiments, different satellites can have different numbers of effectors, especially if some of the satellites have different specialized effectors.

While the highest-level shows the bus as linear, as for example would be the case for satellites disposed along a pacing lead, the satellites could be disposed in a two-dimensional array on a mesh. This is especially practical with one-wire embodiments. This possibility is illustrated with an additional detail view.

Figure 3:
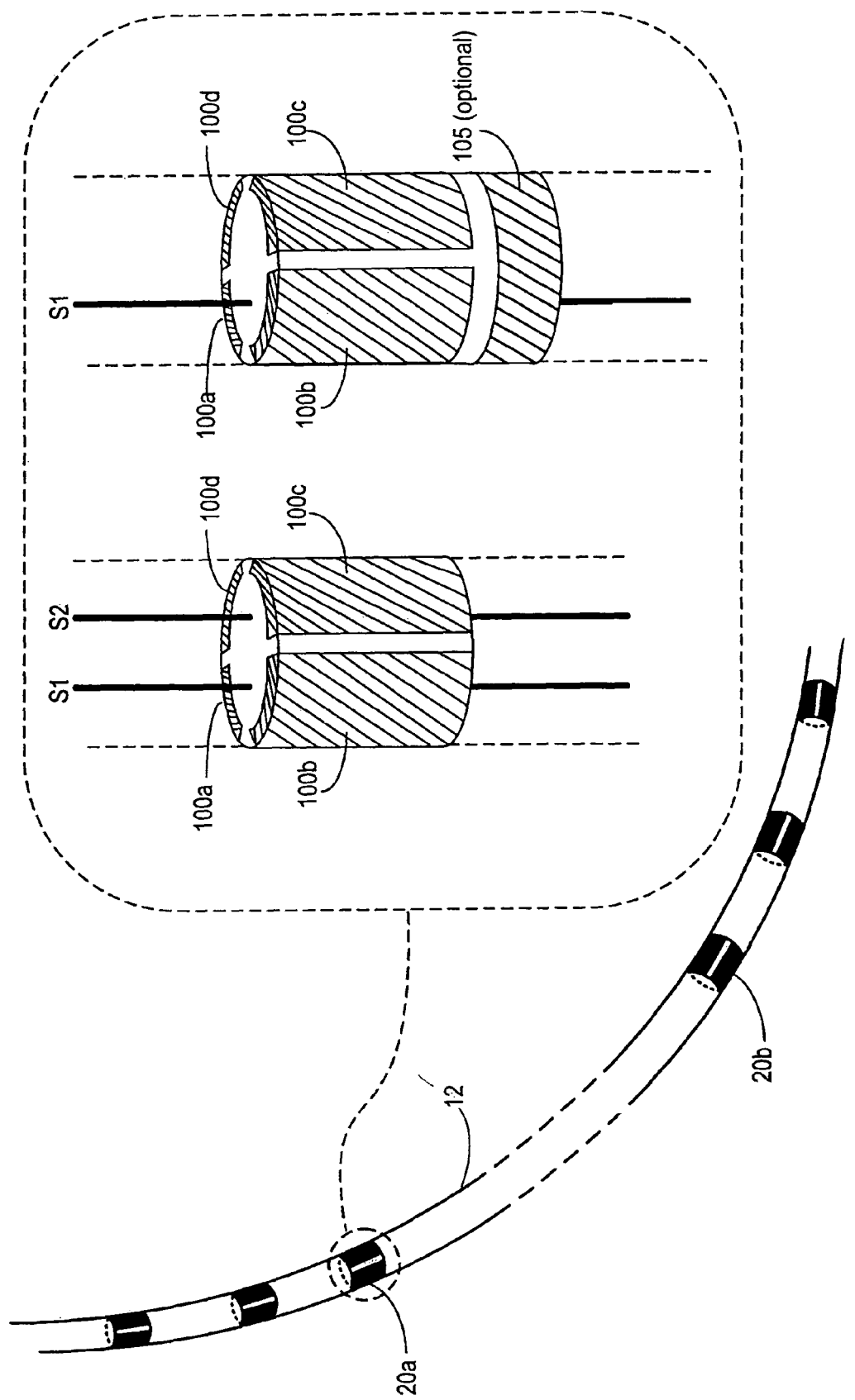
FIG. 3 is an exemplary external view of a lead with several satellites disposed therealong, and also shows enlarged electrode details.

FIG. 3 is an exemplary external view of a lead, say right ventricular lead 12, with several satellites, again denoted 20a, 20b, . . . , disposed therealong. The figure also includes an enlarged detail view of an exemplary electrode configuration for two-wire and one-wire embodiments. The two-wire embodiment is on the left of the detail view, the one-wire embodiment on the right. In this embodiment, the satellites are cylindrical, and at least for the two-wire embodiment are provided with four electrodes, again designated 100a, 100b, 100c, and 100d, configured in the four quadrants of the cylindrical outer walls of satellite 20a. The satellite chip is embedded inside the cylinder and is not shown in this figure. Bus conduction paths S1 and S2 pass through the region between the electrodes and are coupled electrically to the S1 and S2 terminals of the satellite chip. The satellite chips in the satellites receive signals over the bus, which in an exemplary embodiment include address information specifying a given satellite and configuration information specifying which, if any, of electrodes 100a . . . 100d are to be coupled to bus conduction paths S1 or S2.

Although shown in a cylindrical arrangement, electrodes 100a . . . 100d may be offset along lead 12 to minimize capacitive coupling among these electrodes, if desired. The quadrant arrangement of electrodes allows administering pacing current via electrodes oriented at a preferred direction (e.g., away from nerves, or facing an electrode configured to sink the pacing current). Such precise administration of pacing current allows low-power pacing and minimize tissue damage due to the pacing signal.

In the one-wire embodiment, there is only one explicit conduction path that is insulated from the subject's body, namely S1, and the conductive fluids in the subject's body tissues provide the second conduction path S2 (not explicitly shown). In one implementation of a one-wire satellite, a fifth electrode 105 is coupled to the satellite chip's S2 terminal. As described in greater detail below, one of the other electrodes can be used for this purpose.

Representative Timing Diagram

Figure 4:
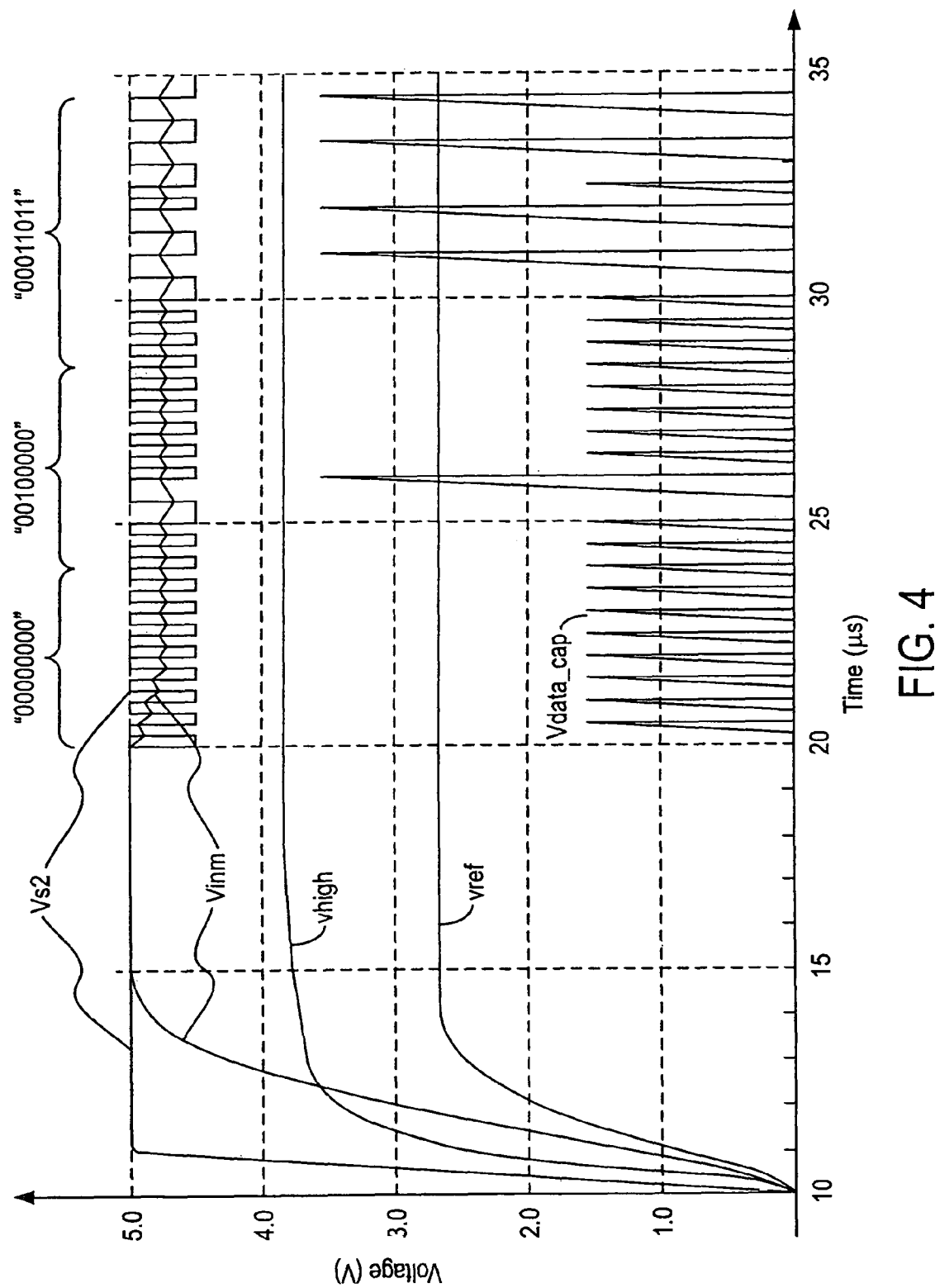
FIG. 4 is a timing diagram showing selected voltage traces of signals on the bus and signals generated on the satellite chip.

FIG. 4 is a timing diagram showing selected voltage traces of signals on the bus and signals generated by DCR circuit 70 in the satellite chip. These voltages are designated "Vs2," "Vinm," "vhigh," "vref," and "Vdata_cap." As mentioned above in connection with FIG. 2, "vhigh" is a voltage stored on capacitor 98 in power recovery circuit 95, being originally derived from the voltage on bus conduction path S2. As will be described in greater detail with reference to FIGS. 7 and 8, DCR circuit 70 includes a local voltage generation circuit 110 and comparators 112 and 115. The DCR circuit's local voltage generation circuit provides a series of voltages "vdcr," "vpbias," "vnbias," and "vref" that are used in the DCR circuit.

More specifically, FIG. 4 shows the result when a DC voltage is supplied on bus 50 and then modulated to communicate data to the satellites. Any suitable modulation regime can be used, such as phase-shift-keying (PSK), frequency-shift keying (FSK), or return-to-zero (RZ), to name a few. In the particular implementation, a data bit is represented by one cycle of a square wave, with a logical "1" having twice the period (represented by a 1-μs cycle) of a logical "0" (represented by a 0.5-μs cycle). This is akin to a type of frequency shift keying (FSK) since the frequency of the square wave differs for the two possible bit values.

The figure shows a particular sequence of bit values encoded as a modulation of the bus voltage, and the voltages generated on the satellite chip to extract these data values. As mentioned above, in a particular implementation, the first conduction path S1 is ground, and therefore the voltages and signals on the chip are generally derived from the voltage on the second conduction path S2.

"Vs2" is the voltage seen by the satellite chip's circuitry by virtue of the voltage on bus conduction path S2. In two-wire configurations, this is the voltage on conduction path S2; in at least some one-wire configurations, it is a diode drop below the potential at an electrode that contacts a biologic conductor (tissue or blood). FIG. 2, as well as a number of figures containing circuit schematics discussed below, use a node label "S2" to represent a coupling to bus conduction path S2. In view of the possibility that the voltage seen at this node might be a diode drop below the value of the voltage on bus conductor these node labels should be read generally to mean "vS2."

"Vinm" is a signal that represents the near-term average of "Vs2." "Vinm" and "Vs2" are the inputs to comparator 112, and are used to produce the clock signal. "vref" is one of the signals generated by the DCR circuit's local voltage generation circuit 110, and is used in connection with the data recovery. To determine the data value, the clock signal is then used to generate a ramp voltage ("Vdata_cap") which is compared to "vref" by comparator 115. If "Vdata_cap" is greater than "vref," the output of comparator 115 becomes a logical "1."

According to some embodiments of the present invention, signal communication on the bus may be conducted in one or more of three phases, namely a configuration phase, a pacing (or other activation) phase, and a signal collection (monitoring) phase. During a configuration phase, central controller 10 sends configuration signals to specify which satellite or satellites to activate and which electrodes on each activated satellite are to be coupled to which bus conduction path (i.e., S1 or S2). The configuration signals, which include various addresses and control commands, are provided to all satellites over bus conduction paths S1 and S2. These configuration signals are communicated by modulating the voltage between bus conduction paths S1 and S2, and in the particular implementation the modulation comprises 0.5 volt peak-to-peak digital pulses on a 5-volt DC signal. This is shown in FIG. 4 as a modulation of signal By way of the example shown in FIG. 4, after an initial time interval of 20 microseconds, during which the signals "Vs2," "vref," and "vhigh" (which are explained in the description corresponding to FIG. 7) are allowed to stabilize, octets "00000000", "00100000" and "00011011" are transmitted with an embedded clock signal ("clk") on bus conduction path S2 (relative to the "ground voltage" of bus conduction path S1). In response, a selected satellite stores the configuration information in its registers and prepares its electrodes to be used for the subsequent pacing or signal collection operations. After the configuration phase (i.e., after the specified satellites are activated and the specified electrodes are coupled to their respective bus conduction paths, or remain disconnected), central controller 10 may initiate a pacing phase or a signal collection phase.

In a pacing phase, central controller 10 sends pacing signals on the bus by generating suitable potential differences between the bus conduction paths. In the pacing phase, pacing occurs at specified configured electrodes to the tissue in their vicinities. Therefore, pacing pulses are delivered during the pacing phase directly and precisely to selected tissue locations.

In a signal collection phase, bus conduction paths S1 and S2 may be allowed to float, so as to conduct analog signals detected by the configured electrodes to central controller 10. Furthermore, the configured electrodes retain their respective configured states (i.e., coupled to or de-coupled from a bus conduction path). Because of the low power consumption of the satellite chips, frequent refreshing of their configurations are not required.

In the two-wire embodiments, the digital control (e.g., configuration) signals and the sensed analog signals are communicated along bus conduction paths S1 and S2. Since both digital and analog signals are communicated along bus conduction paths S1 and S2, it is not necessary to provide the satellites with digital-to-analog or analog-to-digital converters. This reduces the power consumption of the chip, although there may be applications where such conversion circuitry could be provided for special, possibly infrequent use.

In the two-wire embodiments, pacing pulse signals may be applied to the dedicated bus conduction paths S1 and S2, and the voltage applied to the subject's tissue between selected electrodes, either on the same satellite, or on different satellites. However, there are some situations where the pacing voltage would be applied between a selected electrode on a selected satellite and the pacemaker can. While the stimulation provided in this regime is not as localized, it has the advantage that the pacemaker can provides a larger surface than would be provided by a second electrode, thereby reducing the incidence of corrosion.

In one-wire embodiments, where bus conduction path S2 is the subject's body, the digital signals and the pacing signals are communicated through the subject's body.

Satellite Circuitry Overview

Figure 5:
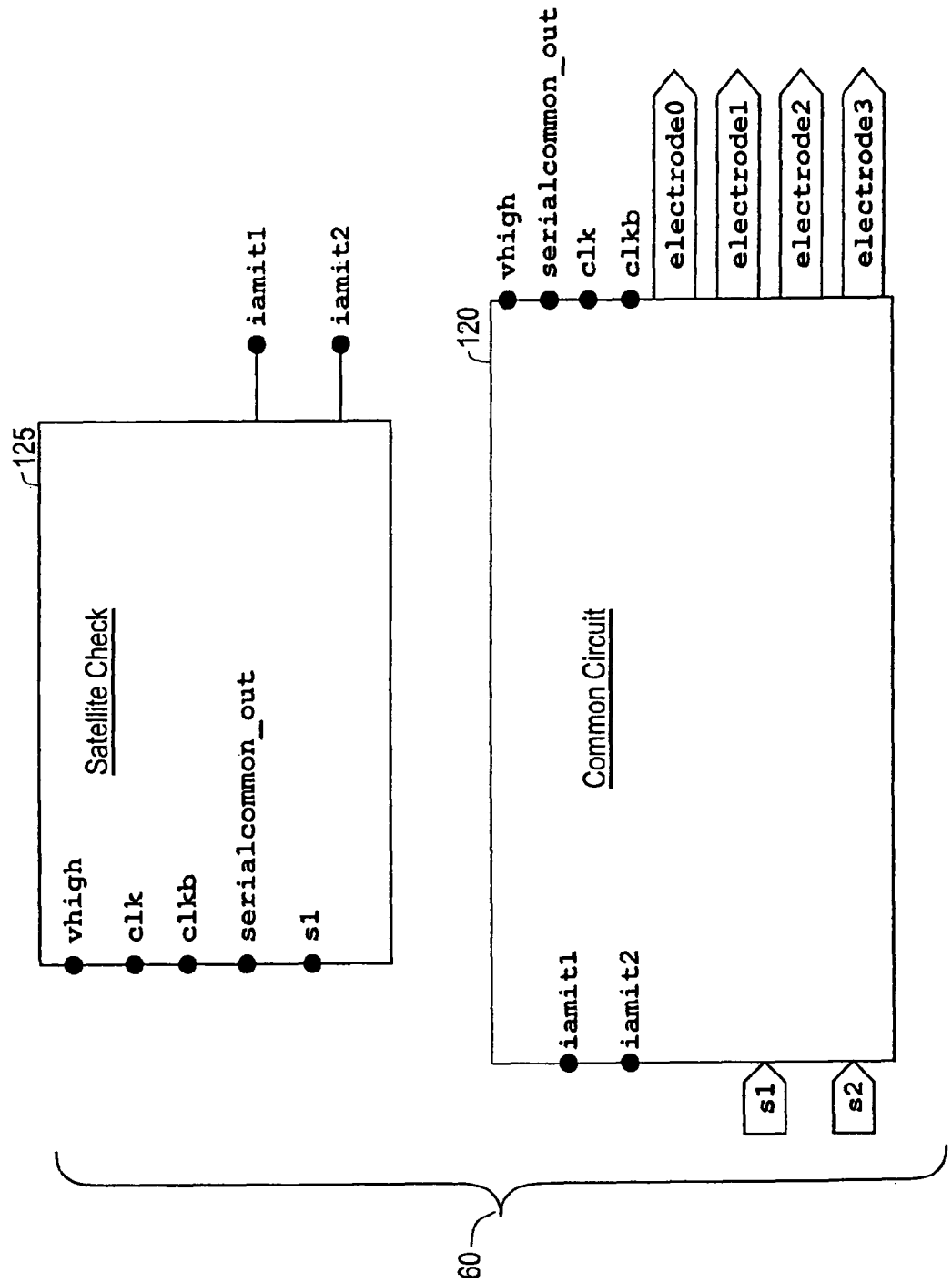
FIG. 5 is a block diagram showing two portions, a satellite check portion and a common portion, of an integrated circuit ("satellite chip") in a satellite.

FIG. 5 is a block diagram of an exemplary embodiment of satellite circuitry 60, as implemented in a satellite chip. As shown in FIG. 5, the satellite chip includes a common circuit 120, which is usually the same for a plurality of satellites, and a satellite-check circuit 125, which is usually different for each satellite. According to one embodiment, common circuit 120 is coupled to bus conduction paths S1 and S2 and is provided identically in each satellite. Common circuit 120 carries out such functions as deriving power supply signal "vhigh," recovering a clock signal (provided as a pair of complementary clock signals "clk" and "clkb") and data bits from signal "Vs2," decoding address signals and control commands, and configuring the electrodes. Common circuit 120 provides decoded address bits serially to satellite-check circuit 125 as a serial output signal "serialcommon_out."

Satellite-check circuit 125 maintains the satellite's unique identity information (address), which is typically hard coded in the chip. It compares the address bits received from common circuit 120 to its stored identity information to derive control signals "iamit1" and "iamit2," which indicate whether or not the received address bits match the identity information stored in satellite-check circuit 125. As described below, control signals "iamit1" and "iamit2" are used to derive configuration signals to configure the electrodes in a satellite for subsequent pacing or signal detection phases.

In one embodiment of the present invention, the functions of a satellite chip mentioned above are carried out by customized digital circuits (combinatorial logic) rather than by executing software or firmware. This approach provides the advantages of low-power operation and fast response time.

Figure 6:
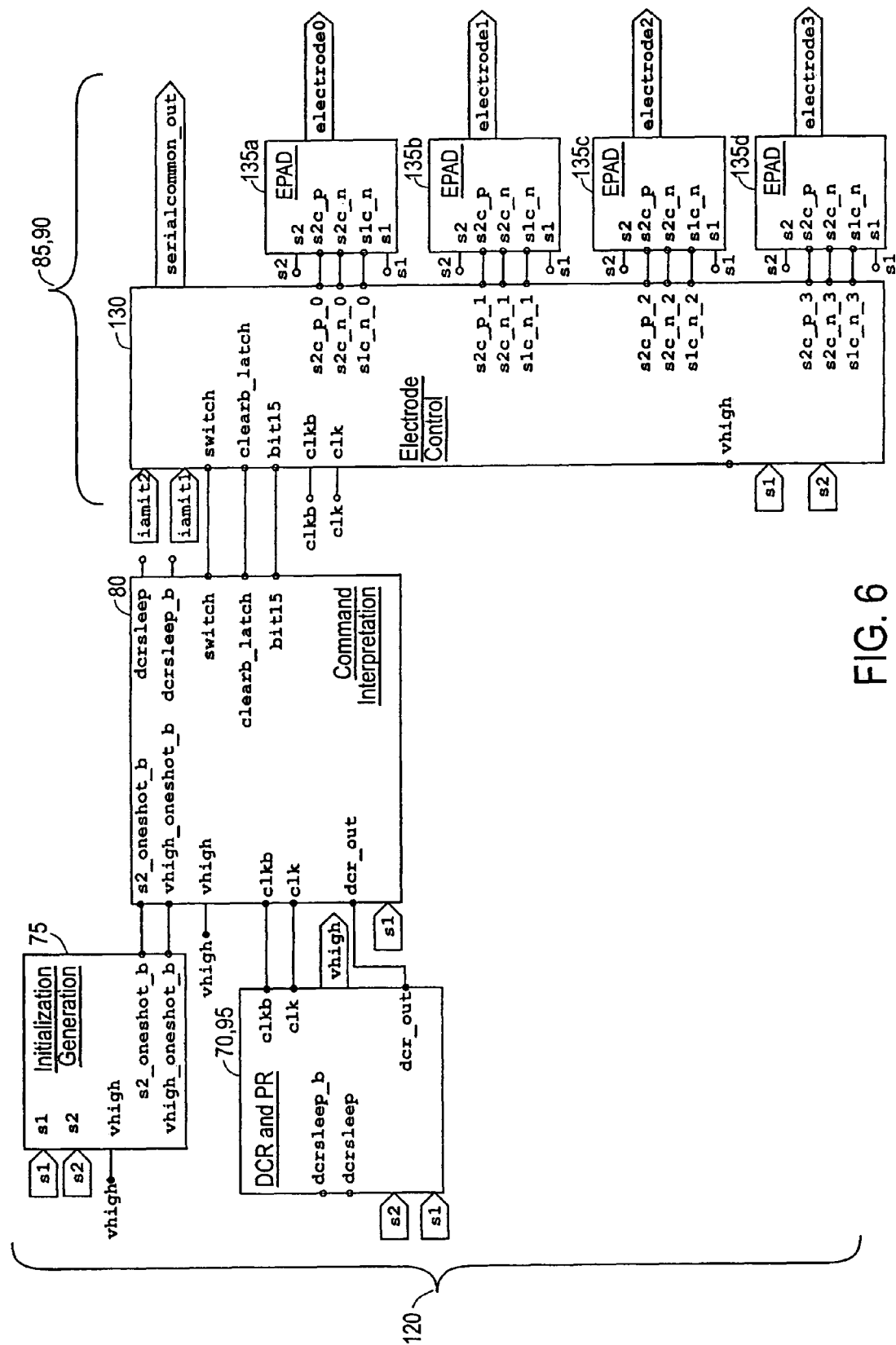
FIG. 6 is a functional block diagram of the common circuitry shown in FIG. 5, showing a data and clock recovery circuit, an initialization generation circuit, a command interpretation circuit, a power recovery circuit, an electrode control circuit, and four electrode switch or electrode pad ("EPAD") circuits.

FIG. 6 is a functional block diagram of an implementation of common circuit 120 of FIG. 5, showing in greater detail the communication among the blocks in FIG. 2. As shown for this implementation, common circuit 120 includes data and clock recovery (DCR) circuit 70, initialization generation circuit 75, command interpretation circuit 80, and power recovery circuit 95. The figure also shows a circuit denoted as electrode control circuit 130 and four circuits denoted as electrode switch or electrode pad ("EPAD") circuits 135a, 135b, 135c, and 135d. Electrode control circuit 130 and EPAD circuits 135a, 135b, 135c, and 135d provide the functionality of electrode registers 85 and electrode driver and switch circuit 90 shown in FIG. 2.

DCR circuit 70 derives and recovers complementary clock signals "clk" and "clkb", and a digital data signal "dcr_out" from the voltage across bus conduction paths S1 and S2. Signal "dcr_out" is a digital signal using 0 volts and voltage "vhigh" to encode logic states of the output bits. DCR circuit 70 also receives complementary sleep signals "dcrsleep" and "dcrsleep_b," which turn off DCR circuit 70 at times when there are no data or clock signals that need to be recovered from the bus, such as during pacing and signal collection phases, or when the satellite has determined that it is not being addressed by digital signals on the bus. Power recovery circuit 95, drawn schematically as part of the same block as DCR circuit 70, derives and recovers the power supply voltage "vhigh" from the voltage across bus conductors S1 and S2. This supply voltage is used to operate the digital circuits in the satellite chip.

Initialization generation circuit 75 derives initialization signals "s2_oneshot_b" and "vhigh_oneshot_b" from the voltage across bus conduction paths S1 and S2. These initialization signals are asserted when "Vs2" and signal "vhigh" rise above their respective predetermined voltage thresholds.

Command interpretation circuit 80 receives the bits in digital data signal "dcr_out" from DCR circuit 70 and maps these bits to control commands. Based on these control commands, it generates control signals designated "switch" for effectuating the configurations specified for the electrodes, "clearb_latch" for clearing the registers, storing the configurations of the electrodes in electrode control circuit 130, and "dcrsleep" and "dcrsleep_b" for turning off DCR circuit 70. Command interpretation circuit 80 also provides the decoded data bits "bit15" (delayed by 16 clock periods) of serial data signal "dcr_out" to electrode control circuit 130. When signal "s2_oneshot_b" is asserted, command interpretation circuit 80 de-asserts signal "dcrsleep" to wake up DCR circuit 70.

When "vhigh_oneshot_b" is asserted, command interpretation circuit 80 asserts signal "clearb_latch" to reset the configuration of the electrodes.

Electrode control circuit 130 receives control signals "switch," "clearb_latch," and "bit15" from command interpretation circuit 80, and control signals "iamit1" and "iamit2" from satellite-check circuit 125, and uses these control signals to identify and configure the electrodes. Electrode control circuit provides output signals "s2c_p_i," "s2c_n_i," and "s1c_n_i" of electrode control circuit 130 are provided to each of four EPAD circuits 135a, 135b, 135c, and 135d (where i is an integer between 0 and 3, inclusive, identifying a corresponding EPAD circuit). Based on the three control signals received, each EPAD circuit is configured to couple to at most one of bus conduction-paths S1 and S2. Electrode control circuit 130 provides the serial data bits to satellite-check circuit 125 as signal "serialcommon_out."

Power Recovery Circuit 95

Figure 7:
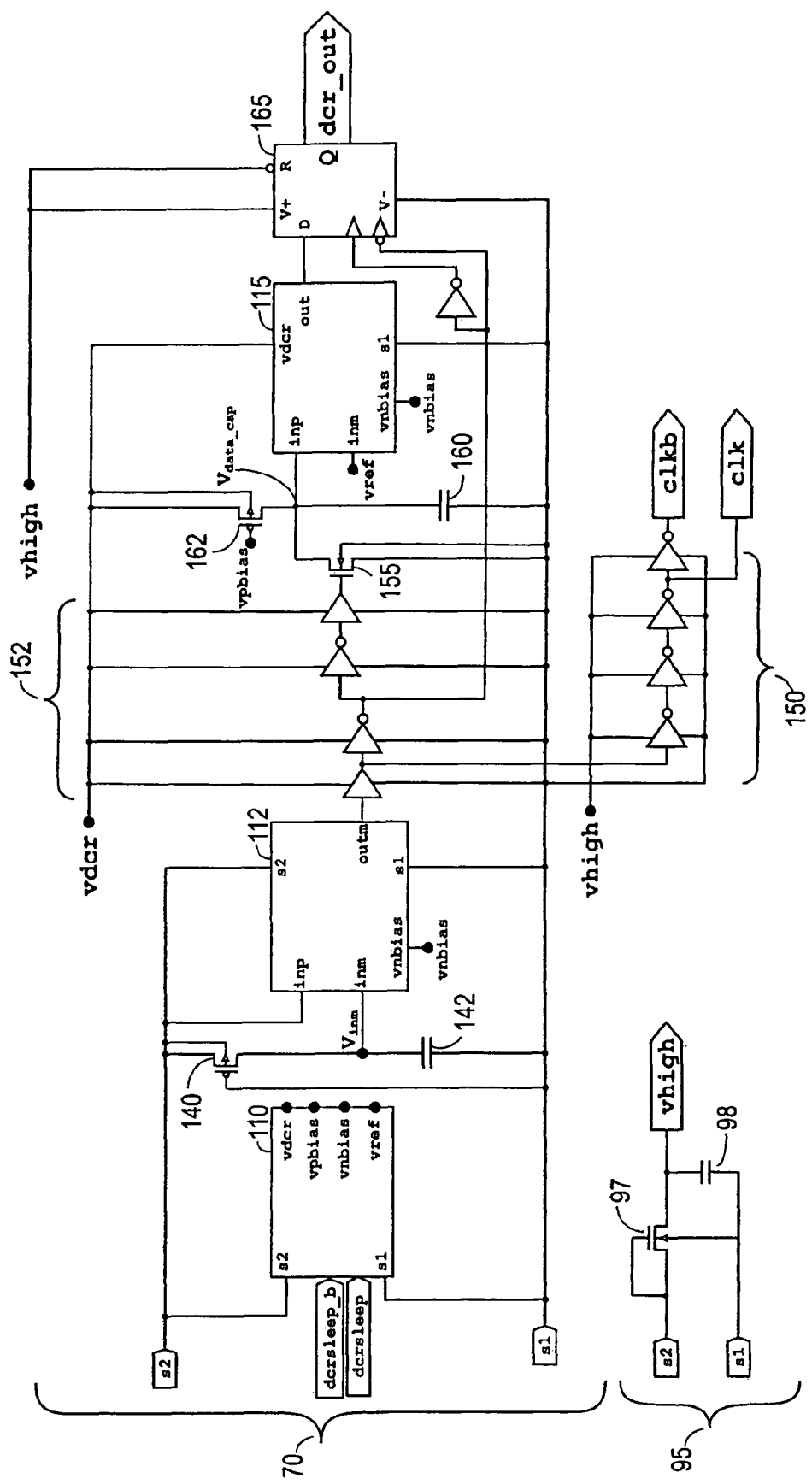
FIG. 7 is a schematic circuit diagram of an exemplary implementation of the data and clock recovery (DCR) circuit and the power recovery circuit shown in FIGS. 2 and 6.

The lower portion of FIG. 7 is a schematic circuit diagram of an exemplary implementation of power recovery circuit 95. As mentioned above in connection with FIG. 2, power recovery circuit includes diode-connected NMOS transistor 97, which charges capacitor 98 to provide power supply voltage "vhigh,", which is used as a high-voltage power supply voltage throughout the satellite chip. In one embodiment of the present invention, the capacitance of capacitor 98 is provided to be greater than about 1200 pF. Note that, as shown in FIG. 4, because of the modulation imposed upon the 5V DC voltage on bus conduction path S2, and because of the voltage drop over diode-connected NMOS transistor 97, power supply voltage "vhigh" is typically lower than 5V.

The present invention also obviates the need for high power dissipation circuits such as A/D and D/A converters. In particular, sleep states are implemented in those logic circuits which are inactive during pacing and data collection phases, or during those intervals where no voltage is being applied to the bus. Hence, the amount of leakage current in the satellite chip is very small. Consequently, power supply voltage "vhigh" needs not be refreshed for long periods of time. In one embodiment, power supply voltage "vhigh" needs not be refreshed more frequently than once every 30 minutes, drawing a current of a few picoamps, so that the resulting power dissipation of the satellite chip is less than a few picowatts. Power supply voltage "vhigh" is used to maintain the states of the registers storing the electrode configurations during those times when the satellite chip is not getting power over the bus.

Data and Clock Recovery (DCR) Circuit 70

The upper portion of FIG. 7 is a schematic circuit diagram of an exemplary implementation of DCR circuit 70. As mentioned above in connection with FIG. 4, the DCR circuit includes a local voltage generation circuit 110 and comparators 112 and 115. The DCR circuit's local voltage generation circuit provides a series of voltages "vdcr," "vpbias," "vnbias," and "vref" that are used in other portions of the DCR circuit. The DCR circuit's local voltage generation circuit will be described in greater detail below with reference to FIG. 8.

Comparator 112 recovers clock signals "clk" and "clkb" from "Vs2" and signal "Vinm." Signal "Vinm," which is generated by a diode-connected PMOS transistor 140 charging a capacitor 142, represents the average value of "Vs2" and has a value substantially between 4.5V and 5V. In one embodiment of the present invention, the capacitance of capacitor 142 is about 5 pF. Because both input signals to comparator 112 are at voltage levels close to 5V, comparator 112 is provided bias voltage "vnbias" which is generated in DCR circuit's local voltage generation circuit 110, shown in detail in FIG. 8.

In view of the nature of the inputs to comparator 112, its output signal "outm" has a time-sequence of pulses corresponding to the modulated digital signal carried on the bus (corresponding to "Vs2"). A set of buffers 150, powered by voltage "vhigh" and referenced to the voltage on bus conduction path S1, provide stable output clock signals "clk" and "clkb," each having a peak-to-peak voltage close to 5 volts. As mentioned above, output clock signals "clk" and "clkb" are distributed throughout the satellite chip as system clock signals. The embedded FSK modulated data signal results in a non-uniform duty-cycle for clock signals "clk" and "clkb."

Output signal "outm" is also buffered by a set of buffers 152. The output signal of buffers 152 drives an NMOS transistor 155. Supply voltage "vdcr" charges a capacitor 160 through a PMOS transistor 162, but NMOS transistor 155 discharges capacitor 160 at each falling edge of signal "outm." When supply voltage "vdcr" charges capacitor 160, signal "Vdata_cap" on capacitor 160 increases linearly before falling back to zero volts at the falling edge. The capacitance of capacitor 160 is chosen such that signal "Vdata_cap" does not exceed reference voltage "vref" during a 0.5-μs cycle (representing logic value "0"), but exceeds reference voltage "vref" during a 1-μs cycle (representing logic value "1").

Thus, by comparing signal "Vdata_cap" with reference voltage "vref," which is selected to be between 2.0 volts and 3.0 volts, as shown in FIG. 4, comparator 115 decodes the data bits embedded in signal "Vs2." The decoded bits in the bit sequence are each captured by a flip-flop 165 at the falling edge of each cycle. Because of the time required for the integration, a one-cycle delay exists between the beginning of the corresponding modulation period for any bit and the time at which decoding for that bit completes.

The negative input signal "Vinm" of comparator 112 decreases from 5V at the beginning of the modulation, but remains approximately at the middle point between 4.5 V and 5 V after the first octet. Hence, comparator 112 is able to generate an accurate clock signal by comparing signal "Vinm" as a reference signal against "Vs2." Accordingly, it is preferred to send an octet of all zeros before relying on the value of "Vinm" as a reference for the clock and data signals. When power from the bus is withdrawn (i.e., "Vs2" goes to zero), the state of flip-flop 155 is preserved, "clk" remains at "vhigh," and "clk" remains at zero since the flip-flop and buffers 150 are powered by "vhigh."

The particular FSK-like modulation regime has the property that the waveform for a "1" bit has twice the area as the waveform for the "0" bit and thus charges capacitor 160 above threshold only for the "1" bit. However, the regime does result in non-uniform clock cycles. One alternative modulation regime that would also work for the same circuitry but provide a uniform clock cycle is as follows. The bit cycle would be constant, but the waveform for a "1" bit would stay high longer, say twice as long, as the waveform for a "0" bit. This bears some resemblance to a phase-shift-keying (PSK) regime.

DCR Circuit's Local Voltage Generation Circuit 110

Figure 8:
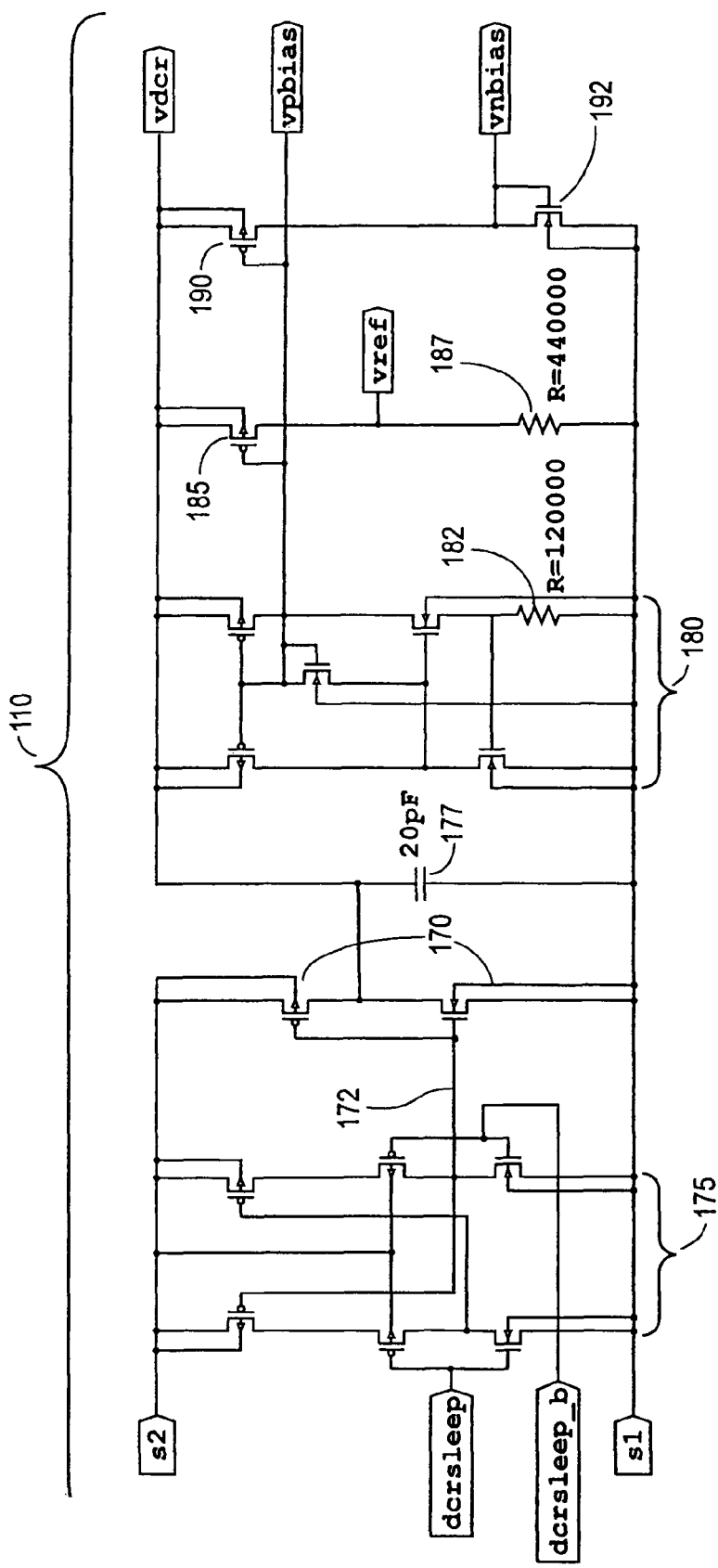
FIG. 8 is a schematic circuit diagram of an exemplary implementation of the DCR circuit's local voltage generation circuit shown in FIG. 7.

FIG. 8 is a schematic circuit diagram of an exemplary implementation of DCR circuit's local voltage generation circuit 110. As mentioned above in connection with FIGS. 4 and 7, the DCR circuit's local voltage generation circuit generates voltages "vdcr," "vpbias," "vnbias," and "vref" for use in other portions of DCR circuit 70.

Voltage "vdcr" is a power supply voltage for use in portions of the DCR circuit, and is generally commensurate with "vS2" unless qualified by the assertion of "dcrsleep," in which case it is pulled low, thereby preventing the DCR circuit from outputting the clock and data signals. When "Vs2" goes to zero, local voltage generation circuit 110 and comparator circuit 112 are powered down, and "vdcr" also goes to zero, thereby powering down comparator circuit 115. Turning off the power to these circuits significantly reduces leakage current during the pacing and signal collection phases when it is no longer required to recover clock and data from "Vs2". Use of the sleep functionality allows "vdcr" to be set to zero, regardless of "Vs2." This provides additional power saving.

Supply voltage "vdcr" is provided at the output of an inverter 170, which receives at an input node 172, the output of a latch 175. Latch 175 stores the values of complementary control signals "dcrsleep" and "dcrsleep_b." When node 172 is at a high voltage, corresponding to signal "dcrsleep" being asserted, the output signal of inverter 170 is coupled to the voltage on bus conduction path S1, thus setting supply voltage "vdcr" to substantially "ground voltage," hence turning off the power supply for the rest of the DCR circuit 70. Alternatively, when control signal "dcrsleep" is de-asserted, as for example during a configuration phase, inverter 170 couples power supply voltage "vdcr" to "Vs2," as averaged or integrated by a capacitor 177.

The DCR circuit's local voltage generation circuit generates the other voltages using a bias generation circuit 180, When control signal "dcrsleep" is de-asserted, thereby bringing "vdcr" to its high level, bias generation circuitry, the current in a resistor 182 of bias generation circuit 180 generates the bias voltage "vpbias," which is used in current mirrors to generate other bias voltages. For example, reference voltage "vref" is generated by a reflected current in a PMOS transistor 185 flowing through a resistor 187. Similarly, the bias voltage "vnbias" is generated by the voltage divider formed by transistors 190 and 192 using another reflected current. As noted above, the reference voltage "vref" is used for recovering data bits from the signal on bus conduction path S2 during a configuration phase.

Initialization Generation Circuit 75

Figure 9:
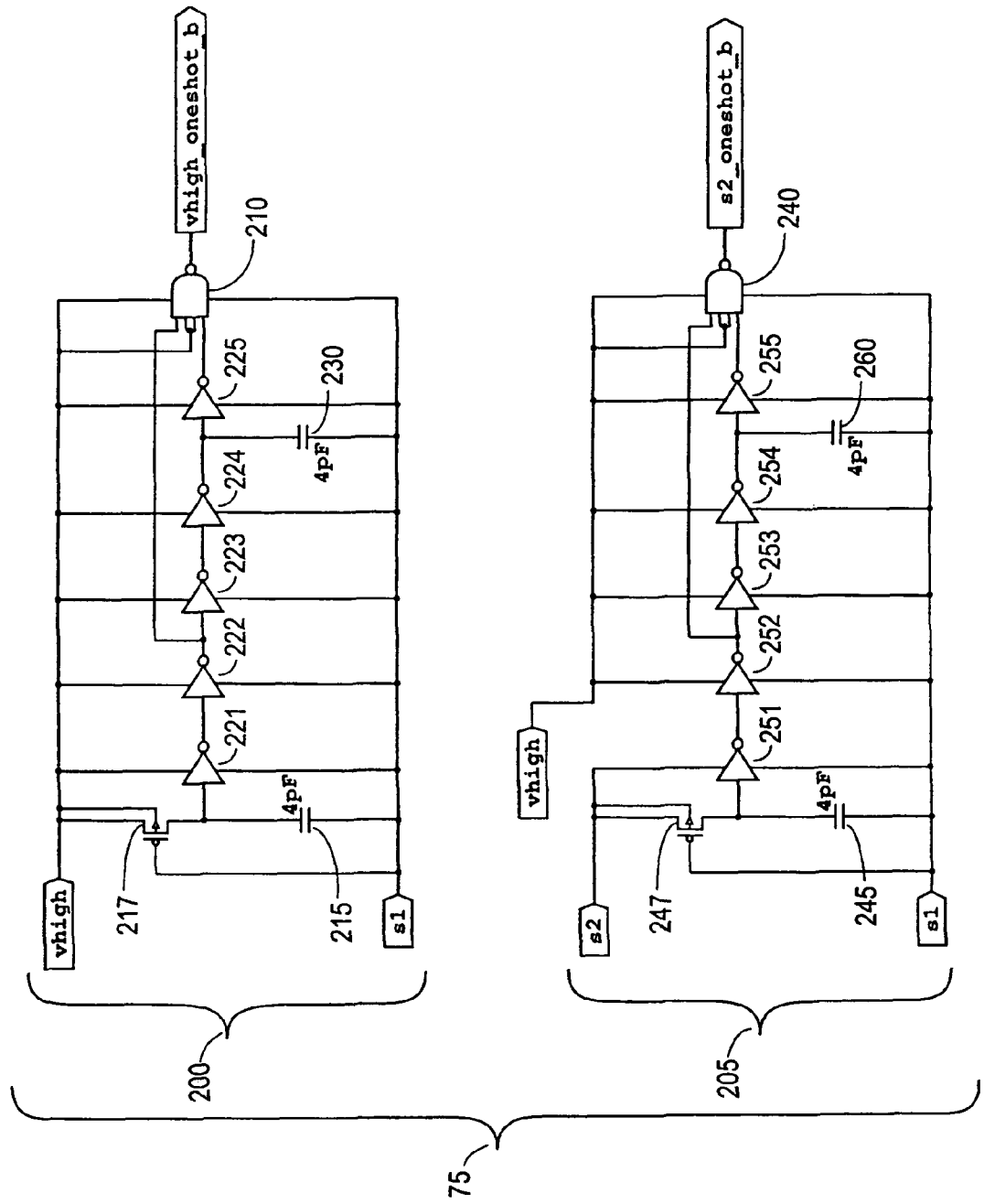
FIG. 9 is a schematic circuit diagram of an exemplary implementation of the initialization generation circuit shown in FIGS. 2 and 6.

FIG. 9 is a schematic circuit diagram of an exemplary implementation of initialization generation circuit 75. As mentioned above in connection with FIG. 6, initialization generation circuit 75 generates initialization signals "s2_oneshot_b" and "vhigh_one_shot_b," which are asserted when the signal on bus conduction path S2 and signal "vhigh" rise above their respective predetermined voltage thresholds. The initialization circuit includes signal generation circuits 200 and 205 that generate "vhigh_oneshot_b" and "s2_oneshot_b," respectively.

Consider initially signal generation circuit 200, which generates initialization signal "vhigh_oneshot_b" at the output of a three-input NAND gate 210. When "vhigh" goes from a low voltage to a high voltage, it charges a capacitor 215 through a diode-connected PMOS transistor 217. The voltage on capacitor 215 is propagated through five inverting buffers 221, 222, 223, 224, and 225 to one of the NAND gate's inputs. The other two inputs are connected to "vhigh" and the output from buffer 222. The output of buffer 224, when high, charges a capacitor 230.

The voltage "vhigh" powers the buffers and the NAND gate, so when "vhigh" is low, all the buffer outputs are low. When "vhigh" increases, the input to buffer 221 remains low for a short period of time before capacitor 215 charges, and the outputs of buffers 221, 222, 223, 224, and 225 will be high, low, high, low, high, respectively. Since the output from buffer 222 is low, the NAND gate will be held at a high level.

However, as capacitor 215 charges, the input to buffer 221 goes above threshold and the output of buffer 221 goes low, the output of buffer 222 goes high, and the output of buffer 225 is still high (its input being held low by capacitor 230 while the capacitor charges). This causes the output of NAND gate 210 to go low. Eventually, capacitor 230 charges and the output of buffer 224 goes above threshold, causing the output of buffer 225 to go low. This causes the output of the NAND gate to go high. So long as capacitors 215 and 230 remain charged, the output of the NAND gate remains high since buffer 225 continues to provide a low voltage to the NAND gate. Thus, the net effect is to generate a downward pulse when the voltage "vhigh" rises to a high voltage state.

Consider next signal generation circuit 205, which generates initialization signal "s2_oneshot_b" at the output of a three-input NAND gate 240. When "Vs2" goes from a low voltage to a high voltage, it charges a capacitor 245 through a diode-connected PMOS transistor 247. The voltage on capacitor 245 is propagated through five inverting buffers 251, 252, 253, 254, and 255 to one of the NAND gate's inputs. The other two inputs are connected to "vhigh" and the output from buffer 252. The output of buffer 254, when high, charges a capacitor 260. "Vs2" powers buffer 252, while "vhigh" powers the buffers 251, 252, 253, and 254, and NAND gate 260. The operation of signal generation circuit 205 is substantially the same as that of signal generation circuit 200, which was described above. Thus the operation will not be described other than to note that the result is a downward pulse when "Vs2" rises to a high voltage state.

Command Interpretation Circuit 80

Figure 10:
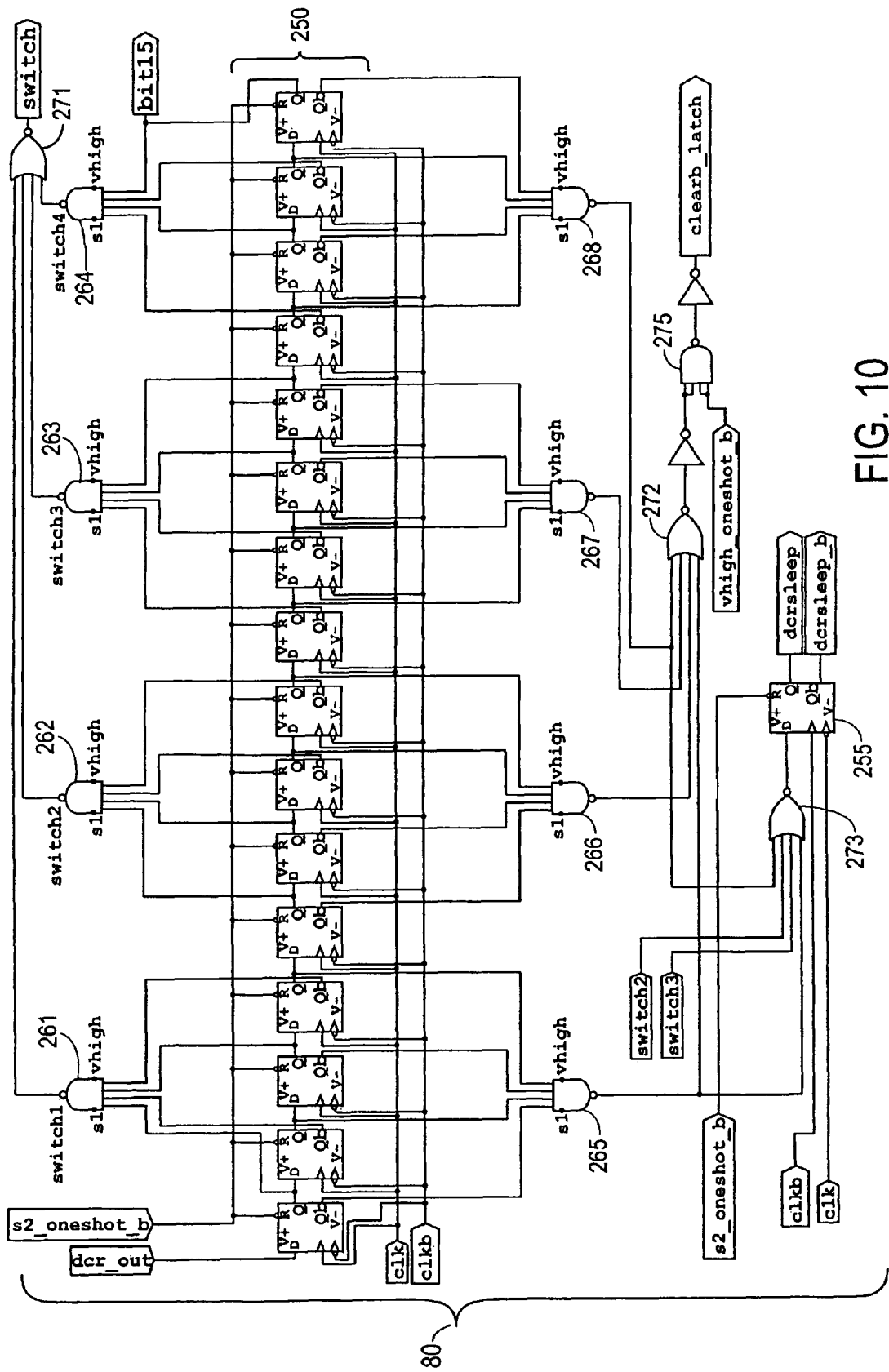
FIG. 10 is a schematic circuit diagram of an exemplary implementation of the command interpretation circuit shown in FIGS. 2 and 6.

FIG. 10 is a schematic circuit diagram showing an exemplary implementation of command interpretation circuit 80. As mentioned above in connection with FIG. 6, command interpretation circuit 80 maps the bits in digital data signal "dcr_out" to control commands, and generates control signals including "switch," "clearb_latch," "dcrsleep," and "dcrsleep_b." Command interpretation circuit 80 provides the decoded data bits ("bit15," delayed by 16 clock periods) of serial data signal dcr_out to electrode control circuit 130.

As shown in FIG. 10, command interpretation circuit 80 includes a 16-bit long serial shift register 250 formed by 16 serially coupled flip-flops. Not shown in the figure for the sake of clarity is the fact that these flip-flops, as well as an additional flip-flop 255, derive power at their respective V+ and V− inputs from "vhigh" and the voltage on bus conductor S1, respectively. The flip flops in shift register 250 are clocked by the clock signals "clk" and "clkb" while flip-flop 255 is clocked by these signals but out of phase. This allows the flip-flop to act on the data that was clocked into the shift register during the previous half cycle.

Predetermined bit patterns in shift register 250 are recognized by a decoding circuit, with a set of NAND gates 261, 262, 263, 264, 265, 266, 267, and 268 directly receiving one or both of the flip-flop's complementary outputs, and a set of NOR gates 271, 272, and 273 receiving various combinations of the NAND gate outputs to produce control signals "switch," "clearb_latch," and the complementary pair of sleep signals "dcrsleep" and "dcrsleep_b." Note that the "switch" signal triggers electrode control circuit 130 to cause one or more specified electrodes to be coupled to either bus conduction path S1 or bus conduction path S2.

As mentioned above, after the configuration phase, sleep signals "dcrsleep" and "dcrsleep_b" turn off portions of the satellite chip to conserve power. In one embodiment of the present invention, the Sleep command corresponds to bit pattern "0101100001111010." The signal "dcrsleep" is generated by the output signals of NAND gates 262, 263, 265, and 268, and NOR gate 273. Flip-flop 255 latches and holds the output of NOR gate 273 to provide the "dcrsleep" and "dcrsleep_b" signals during pacing and/or signal collection phases, during which DCR circuit 70 is in a turned-off state.

The "clearb_latch" signal is generated in part by the output signals of NAND gates 265, 266, 267, and 268, which are communicated to NOR gate 272. NOR gate 272 is provided to one input of a NAND gate 275, and is triggered by the "vhigh_oneshot_b" initialization signal at the other input of NAND gate 275. The "clearb_latch" signal, when asserted, resets the registers in electrode control circuit 130, so as to clear the coupling between the electrodes and bus conduction paths S1 and S2. In one embodiment of the present invention, the Clear command corresponds to bit pattern "10101001111001010." In this embodiment, because relatively few commands are encoded in a large command space (e.g., 16-bit per command), in all likelihood most bit errors would result in a command that is not recognized, and thus would not erroneously activate and configure electrodes to result in unintended pacing.

The "switch" signal is generated by the outputs of NAND gates 261, 262, 263, and 264, and NOR gate 271. This signal is generated in response to detecting a Switch command for effectuating the configurations specified for the electrodes. In one embodiment of the present invention, the Switch command corresponds to bit pattern "1010110000110101."

The "s2_oneshot_b" initialization signal resets all the flip-flops of shift register 250, when the signal "Vs2" rises to 5 volts. Furthermore, the output bit of the last flip-flop in shift register 250 is provided as output signal "bit15." Output signal "bit15" allows the received data bits to be transmitted to electrode control circuit 130 for electrode address information decoding. A circuit similar to the circuit in FIG. 10 is provided in satellite-check circuit 125 to capture a predetermined bit pattern, which is interpreted as an address of the specified satellite. Satellite selection signals "iamit1" and "iamit2" are asserted when the address matches the stored identity information of the satellite.

Electrode Control Circuit 130

Figure 11:
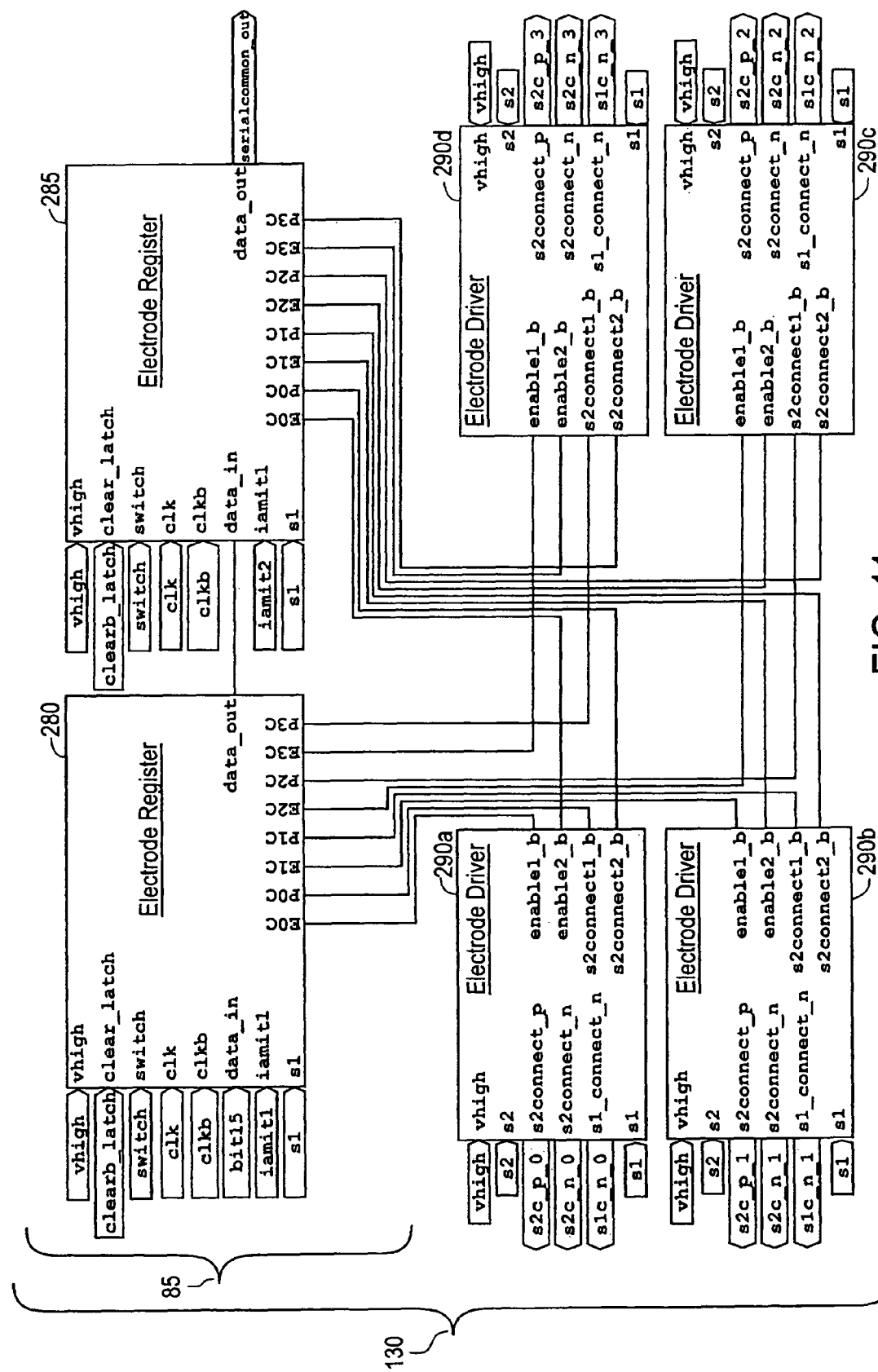
FIG. 11 is a functional block diagram of an exemplary electrode control circuit that includes two electrode register circuits and four electrode driver circuits.

FIG. 11 is a functional block diagram of an exemplary embodiment of electrode control circuit 130. As described above in connection with FIG. 6, electrode control circuit 130 receives control signals from command interpretation circuit 80 and satellite-check circuit 125, and uses these signals to identify and configure the electrodes. The electrode control circuit generates output signals "s2c_p_i," "s2c_n_i," and "s1c_n_i" to control EPAD circuits 135a, 135b, 135c, and 135d, which in turn determine which electrode(s), if any will couple to a given bus conduction path.

In one embodiment of the present invention, control signals "iamit1" and "iamit2" indicate whether or not the local satellite is selected by the system. Central controller 10 then sends electrode address information to the satellite chip. The electrode address information determines which of the electrodes under the control of electrode control circuit 130 are to be coupled to which of bus conduction paths S1 or S2. The system performs the actual coupling after receiving a "switch" command from central controller 10.

As shown in FIG. 11, electrode-control circuit 130 includes two identical electrode register circuits 280 and 285, and four identical electrode driver circuits 290a, 290b, 290c, and 290d. Each of electrode register circuits 280 and 285 receives an 8-bit electrode address information word and a corresponding control signal which is one of identity control signals "iamit1" and "iamit2." The 8-bit electrode address word and identity control signal are decoded to provide four pairs of electrode control signals "EnC" and "PnC" (where n is an integer between 0 and 3 inclusive, identifying one of electrode driver circuits 290a, 290b, 290c, and 290d). These electrode driver circuits drive EPAD circuits 135a, 135b, 135c, and 135d, respectively (shown in FIG. 6, and in more detail below in FIG. 14).

In this implementation, for example, electrode register circuit 280 provides its 8-bit electrode address information word as controls signals E0C, P0C, E1C, P1C, E2C, P2C, E3C, and P3C, respectively, when control signal "iamit2" is asserted. Control signals E0C and P0C are received into electrode driver circuit 290a and denote whether or not electrode driver circuit 290a (and hence its corresponding electrode also) is enabled and its polarity, respectively. Similarly, electrode driver circuit 290a receives another pair of these control signals from electrode register 285. Based on these four control signals (corresponding to signals internally denoted in each electrode driver circuit as "enable1_b," "enable2_b," "s2connect1_b," and "s2connect2_b"), control signals "s2c_p_i," "s2c_n_i," and "s2c_n_i" are provided to control the switching of a corresponding electrode.

One advantage of this design for electrode control circuit 130 is that it allows a selected electrode to be coupled to bus conduction path S1, according to the control signals from electrode register circuit 280, for example. It also allows another selected electrode to be coupled to bus conduction path S2, according to the control signals from electrode register 285. In this manner, one electrode sources current into the tissue, while a another electrode sinks current from the tissue. This arrangement allows the pacing system to focus the pacing current to a specific tissue area. In contrast, a pacing system without a current-sink electrode may suffer from diffusing current over a large tissue volume and unsatisfactory pacing accuracy and efficacy.

While one-wire embodiments would not supply pacing signals between electrodes on the same satellite, the ability to allow any electrode to be coupled to either bus conduction path nevertheless provides flexibility. Further, as noted above, pacing pulses may still be applied between a satellite electrode and the pacing can through the subject's body in two-wire embodiments as well as in one-wire embodiments.

Electrode Control Circuit 130's Electrode Register Circuits 280, 285

Figure 12:
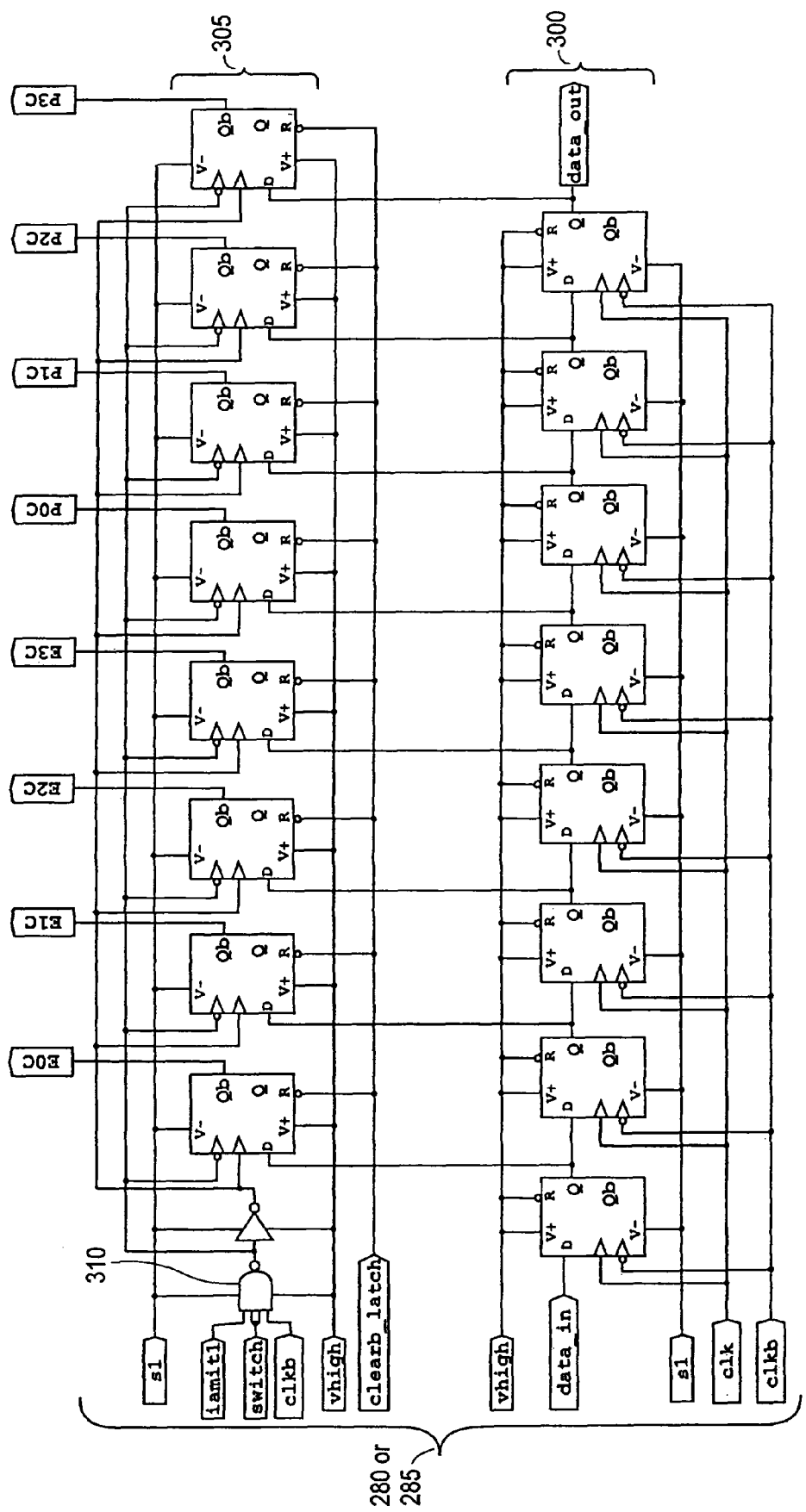
FIG. 12 is a schematic circuit diagram of an exemplary implementation of any one of the electrode register circuits shown in FIG. 11.

FIG. 12 is a circuit schematic of an exemplary implementation for an electrode register circuit (e.g., one of electrode register circuits 280 and 285). The electrode register circuit includes a shift register 300 and a parallel register 305, each comprising eight flip-flops. The flip-flops in shift register 300 are serially coupled and store the incoming data bits in order. Each flip-flop in register 305 loads the output bit of a corresponding flip-flop in the shift register whenever the "switch" signal is asserted. (A previous assertion of signal "clearb_latch" resets the output bits of register 305 to logic value "0.") The "switch" signal is gated (NAND gate 310) by the identity control signal it receives (e.g., control signal "iamit1," if the electrode register circuit implements electrode register 280). In this way, only the correct electrode address information is received by register 305 and is provided as control signals to electrode driver circuits.

Figure 13:
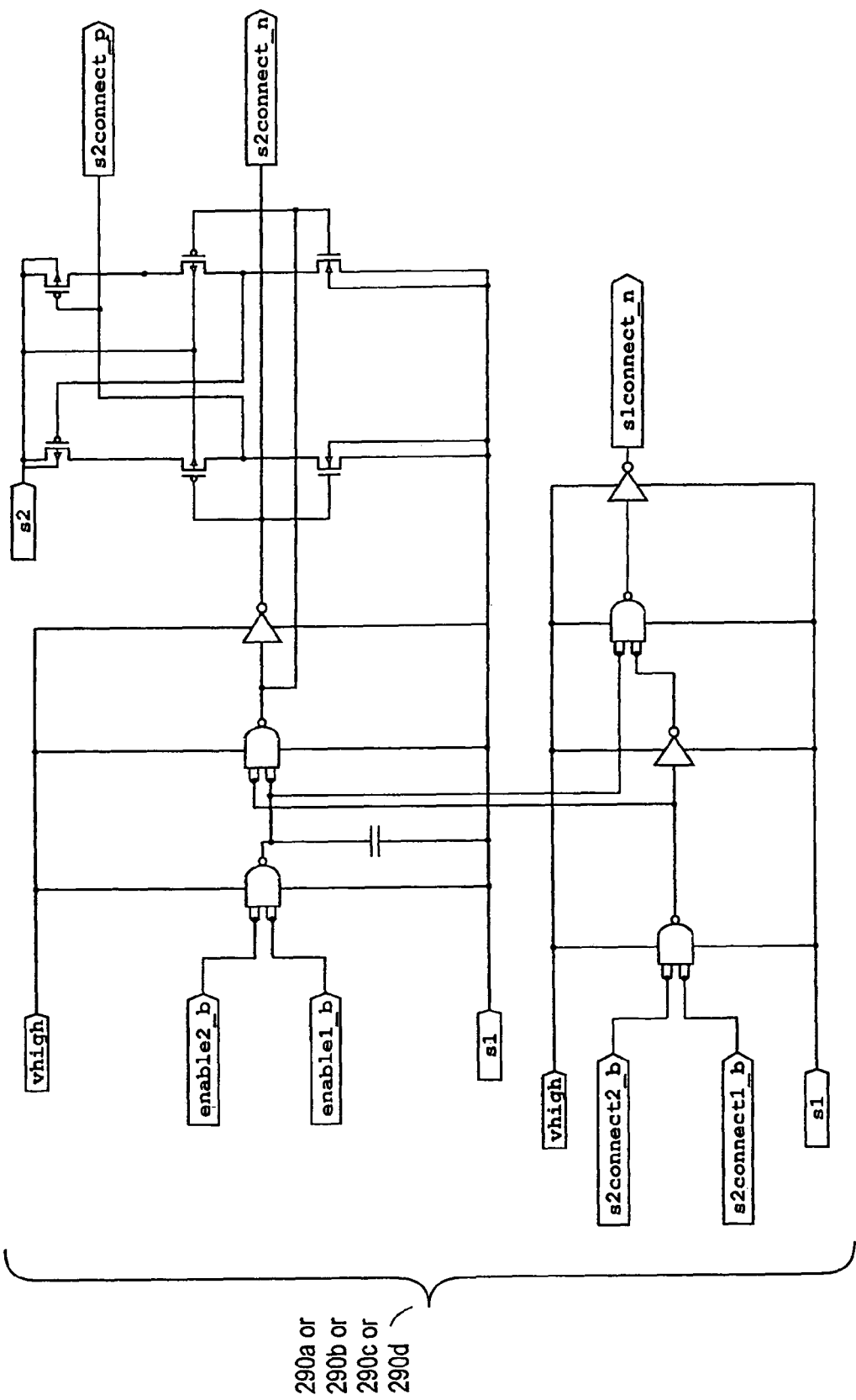
FIG. 13 is a schematic circuit diagram of an exemplary implementation of any one of the electrode driver circuits shown in FIG. 11.

Electrode Control Circuit 130's Electrode Driver Circuits 290a, 290b, 290c, 290d FIG. 13 is a schematic circuit diagram of an exemplary implementation of any one of electrode driver circuits 290a, 290b, 290c, and 290d. The electrode driver circuit receives signals "enable1_b," "enable2_b," "s2connect1_b," and "s2connect2_b," which correspond to signals EnC and PnC from electrode registers in electrode register circuits 280 and 285, respectively. These input control signals are decoded to provide control signals "s1connect_n," "s2connect_n," and "s2connect_p" according to a truth table, which is provided in the following

TABLE 1

| | | | | | | | | |
|---|---|---|---|---|---|---|---|---|
| Input | enable1_b | 1 | 0 | X | 0 | 0 | X | X |
| | enable2_b | 1 | X | 0 | X | X | 0 | 0 |
| | s2connect1_b | X | 1 | 1 | 0 | X | 0 | X |
| | s2connect2_b | X | 1 | 1 | X | 0 | X | 0 |
| Output | s2connect_p | 1 | 1 | 1 | 0 | 0 | 0 | 0 |
| | s2connect_n | 0 | 0 | 0 | 1 | 1 | 1 | 1 |
| | s1connect_n | 0 | 1 | 1 | 0 | 0 | 0 | 0 |
| | EPAD Action (bus conduction path to which electrode is coupled) | Not coupled | S1 | S1 | S2 | S2 | S2 | S2 |

Signals "s1connect_n" and "s2connect_n" assume voltage values corresponding to "vhigh" or 0, while signal "s2connect_p" assumes voltage values of "Vs2" or 0. As mentioned above, "vhigh" is used to maintain the electrode register state during times when the satellite chip is not receiving bus power. In principle, only the flip-flops in parallel register 305 need be maintained, i.e., preserving the values of E0C, P0C, E1C, P1C, E2C, P2C, E3C, and P3C. In a current implementation, however, all the flip-flops are kept energized so that the shift registers don't come up in an unknown state.

EPAD Circuits 135a, 135b, 135c, and 135d

Figure 14:
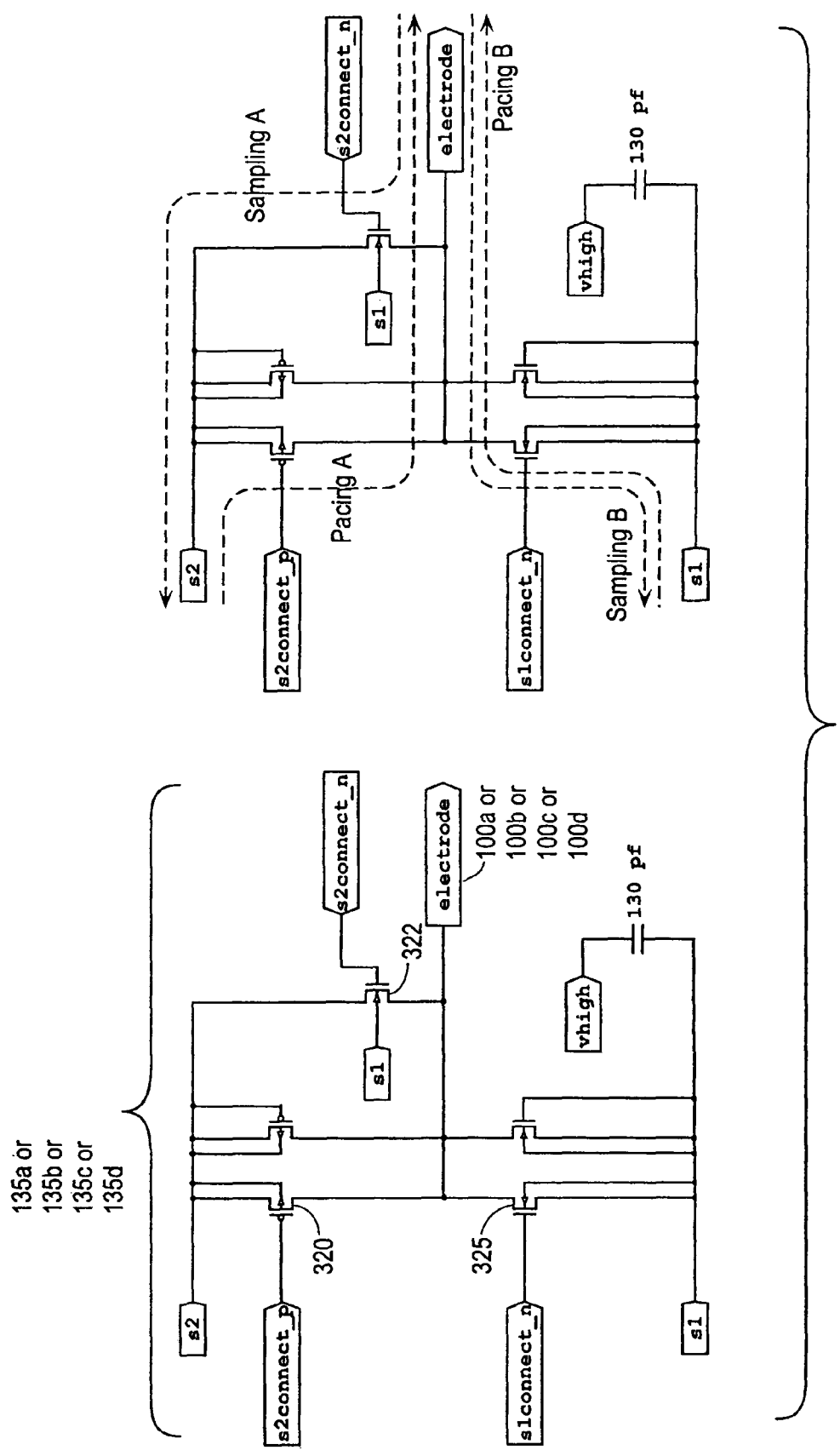
FIG. 14 is a schematic circuit diagram of an exemplary implementation of one of the electrode pad (EPAD) circuits shown in FIG. 6.

FIG. 14 is a schematic circuit diagram of an exemplary implementation of one of the electrode pad (EPAD) circuits shown in FIG. 6. The circuit is drawn separately (and identically) in right and left portions of the figure. The right portion shows current paths for various scenarios, and the reference numerals have been removed for clarity.

The particular mapping shown in Table 1 is designed for the particular EPAD circuit shown in FIG. 14. In Table 1, the values (1, 0, 0), (1, 0, 1) and (0, 1, 0) for signal combination ("s2connect_p", "s2connect_n", s1connect_n") encode instructions to leave the specified electrode uncoupled, to couple the specified electrode to bus conduction path S1, and to couple the specified electrode to bus conduction path S2, respectively.

In the EPAD circuit, a low voltage at signal "s2connect_p" couples the electrode to bus conduction path S2 through a PMOS transistor 320. A high voltage at signal "s2connect_n" couples the electrode to bus conduction path S2 via an NMOS transistor 322. A high voltage at signal "s1connect_n" couples the electrode to bus conduction path S1 via an NMOS transistor 325. Thus, the values (1, 0, 0), (0, 1, 0) and (1, 0, 1) for signal combination ("s2connect_p", "s2connect_n", s1connect_n") decouples the electrode from S1 and S2, couples the electrode to S2, and couples the electrode to S1, respectively.

The right portion of FIG. 14 shows current paths between the electrode and the selected bus conduction path. The different paths are designated "Pacing A," "acing B," "Sampling A," and "Sampling B," depending on the conduction path and the reason for coupling the electrode to the bus conduction path.

For those one-wire embodiments where there is no dedicated fifth electrode to contact the subject's body fluid, one of electrodes 100a ... 100d is used to provide "Vs2" to the chip circuitry. This electrode cannot be coupled to bus conduction path S1. This is shown as the path "Sampling A" and "Vs2" is a diode drop below the voltage at the electrode due to the driver transistor whose gate is at the lower potential "Vs2" compared to the electrode.

System Operation

In a specific embodiment, the configuration and control command structure is as follows. The Sleep command generates sleep signals "dcrsleep" and "dcrsleep_b," which turn off DCR circuit 70 at times when there are no data or clock signals that need to be recovered from the bus. The Clear command generates the control signal "clearb_latch" for clearing the flip-flops in parallel register 305. The Switch command generates the control signal "switch," which loads the values in shift register 300 into parallel register 305. The Switch command is only issued following the transmission of address and configuration information. The current architecture supports configuring any two satellites with a single Switch command.

More particularly, the central controller communicates two satellite identification octets for the two satellites to be configured, followed by two configuration octets representing electrode switching states for the addressed satellites, followed by the Switch command. The serial bit stream from DCR circuit 70 passes through 16-bit shift register 250 in command interpretation circuit 80, thereafter into the two 8-bit shift registers 300 in electrode register circuits 280 and 285, and finally into two similar 8-bit shift registers (not separately shown) in satellite check circuit 125. Thus, when all the bits for the two satellite identification octets, followed by the two configuration octets, followed by the Switch command have been read in, the satellite identification octets are in the satellite check circuit shift registers, the configuration octets are in shift registers 300 in electrode register circuits 280 and 285, and the Switch command bits are in shift register 250 in command interpretation circuit 75.

Thus satellite check circuit 125 is in a position to match each satellite identification octet against that satellite's hard-coded identification and issue the "iamit1" and "iamit2" control signals signifying a match, electrode register circuits 280 and 285 are have the configuration octets in their shift registers, and command interpretation 80 is in a state where the 16 bits in its shift register, when decoded signify that they represent the switch command. Thus, each satellite can determine whether it is one of the satellites to be configured, and if so, allows the "switch" signal to be passed through to load the contents of shift register 300 into parallel register 305.

Figure 15:
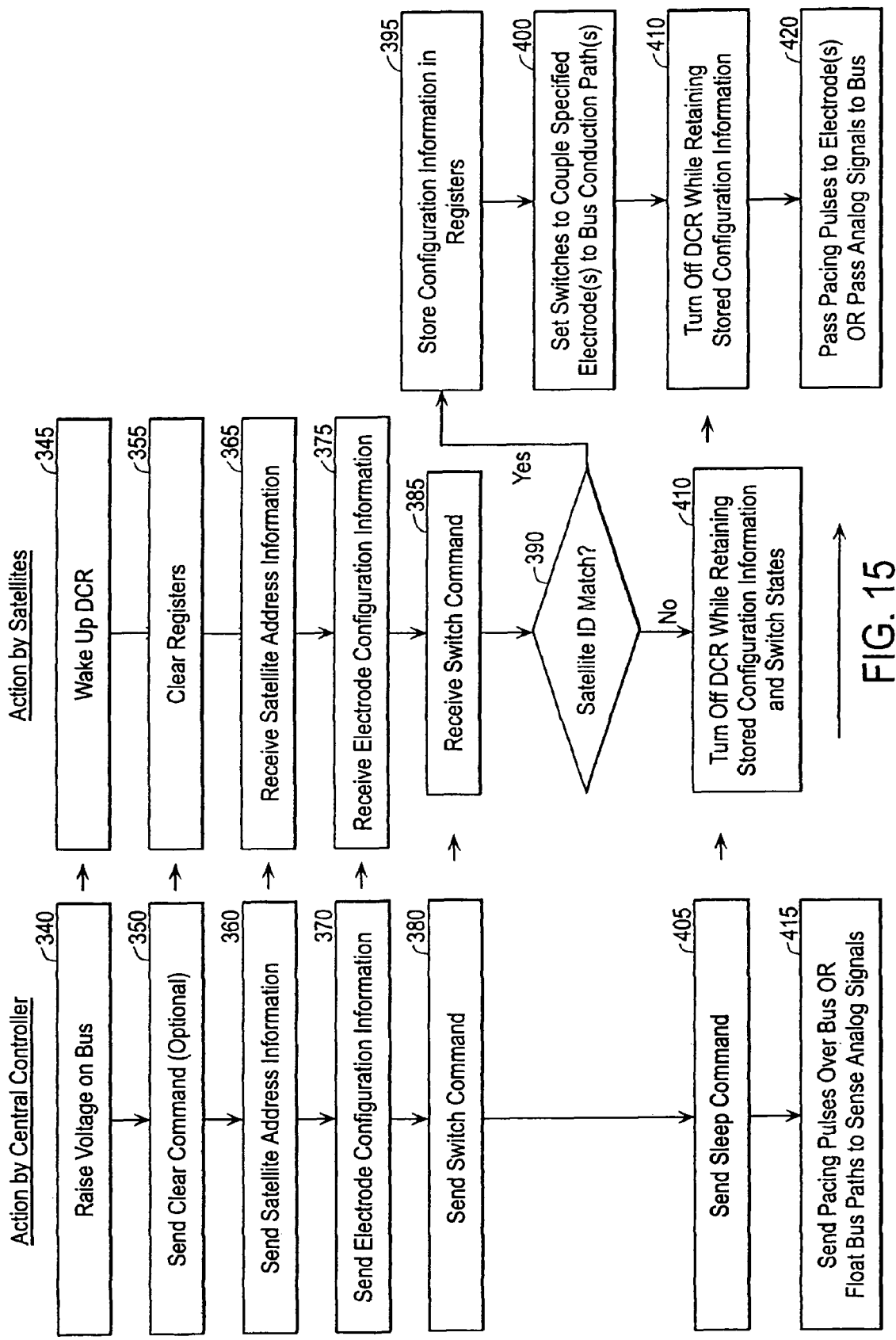
FIG. 15 is a flow chart illustrating an exemplary configuration (programming) process followed by a cardiac pacing or monitoring process.

FIG. 15 is a flow chart illustrating an exemplary configuration (programming) process followed by a cardiac pacing or monitoring process. The flow chart has a left portion showing the operation from the point of view of central controller 10, and middle and right portions showing the operation from the point of view of the satellites. The flow chart shows the operations in a particular order, which is an abstraction. As discussed above, the serial nature of the particular hardware architecture is that the satellite information, the electrode configuration information, and the switch command are passing through the various shift registers and don't represent the operative state until the last bit has been read into the command interpretation shift register.

The central controller commences the process by raising the voltage on bus conductive path S2 (step 340), in response to which the satellites wake up their DCR circuits (step 355), so as to be able to accept and process digital data in some cases the sends the Clear command (step 350), in response to which the satellites clear their registers (step 355). This is optional, but is usually done, especially when configuring more than two satellites.

The central controller initiates a configuration phase by sending satellite address information (step 360), and the satellites receive this information (step 365). In the specific implementation, this entails clocking the serial bit stream into the command interpretation circuit's shift register, which is not the final destination. Rather, the satellite address data is only available in the satellite check circuit's registers after subsequent data is sent and received.

The central controller then sends electrode configuration information (step 370) and the satellites receive this information (step 375). The central controller then sends the Switch command (step 380) and the satellites receive this command. Each satellite then determines whether the received address information matches that satellite's stored satellite address information (branch 390). Those satellites for which the received address information matches that satellite's stored satellite address information (i.e., at least one of control signals "iamit1" and "iamit2" is asserted) store the configuration in their registers (step 395) and set their switches (step 400) to couple the appropriate electrode(s) to the appropriate bus conduction path(s). Steps 360, 370, and 380 (and the responsive steps 365, 375, 385, 390, 395, and 400) may be repeated depending on the number of satellites that are to be configured.

The central controller then sends the Sleep command (step 405), in response to which the satellites turn off their DCR circuitry while retaining stored configuration information (step 410). The central controller then enters a pacing or sensing phase by sending pacing pulses or floating the bus conductive paths and activating sensing circuitry to sense analog signals using the configured electrodes (step 415). Depending on the type of phase, the satellites pass the pacing pulses from the bus to the electrode(s) or pass the analog signals from the electrodes to the bus (step 420). In most cases, the satellites do not need to perform any particular actions during these phases. Many sensing and pacing phases can be implemented between two consecutive electrode configurations. For example, after a configuration is completed, the central controller can sense the impedance between electrodes to verify that the electrodes are properly configured or remains properly configured before each pacing commences.

Exemplary Sensing Application

Because embodiments of the present invention provide exceptional flexibility, various applications beyond cardiac pacing are now possible. One such application is the measurement of the speed at which a depolarization wave propagates within the tissue. The precise measurement of signal conduction velocity can be very useful in assisting other forms of treatments. For example, the ideal dosage of certain medication can be assessed by monitoring different tissue conduction velocities.

It is understood that some medications which are often prescribed to cardiac patients can change the conduction velocity of a depolarization signal propagating in the cardiac tissue. The conduction velocity within the tissue can be used as a feedback measurement for titration of various medications such as beta blockers. Without proper titration, a sub-optimal dosage of medication may result in the heart not contracting enough or contracting too much. Embodiments of the present invention make accurate titration possible. Typically, the propagation delay of a depolarizing signal is much slower (e.g., in the order of milliseconds) than the time required to reconfigure the electrodes (e.g., in the order of microseconds). Note that for conduction-velocity detection purposes, a depolarizing signal is preferred over a signal with a single polarity which uses the patient's body as a current sink. A depolarizing signal is more resistant to interferences and can be localized more accurately. Detection of such a depolarizing signal is possible in embodiments of the present invention because two electrodes within the same satellite can be configured as a pair of bipolar electrodes.

In one exemplary process for measuring conduction velocity using satellites, the electrodes in satellites at different locations along the signal's propagation path may be successively configured to sense the depolarization wave. The conduction velocity may be calculated from the time at which each satellite senses the passing of depolarization wave. The measured conduction velocity can be used to determine the effectiveness of the medicine or to formulate an effective dose.

More specifically, to detect a depolarizing signal (naturally occurring or induced) the system transmits necessary commands and data to configure a first satellite so as to create a pair of bipolar receiving electrodes on the first satellite. When the depolarizing signal reaches the first satellite, the signal is received by the bipolar electrodes and the receiving time is recorded. After recording the time at the first satellite, the system subsequently transmits another set of information to configure a second satellite so as to create a pair of bipolar receiving electrodes on the second satellite. When the propagating signal reaches the second satellite, the system receives the signal and records the corresponding time. Based on the respective times at which the first and second satellites detect the signal, the system can calculate the propagation delay between the two satellites, and based on the separation of the satellites, can calculate the signal's conduction velocity.

Another application allows a large number of sensing phases to be provided over a very short period of time between configuration phases involving different combinations of electrodes in the satellites. Such rapid sensing and reconfiguration allows a signal map be drawn over that short period of time for any major electrical event in the vicinities of the satellites in the lead.

Two-Wire Programming and Pacing

FIG. 16A is a schematic representation of programming and pacing with a two-wire embodiment of the invention. The figure shows central controller 10 and a single satellite, designated 20 (it could be any of satellites 20a . . . 20d in FIG. 2). The central controller and the satellite have corresponding S1 and S2 terminals (nodes), and the connection between the central controller and the satellite is through two bus conduction paths having dedicated conductors that are insulated from the subject's body. The left portion of the figure shows the current path for programming the satellite. The current flow is shown schematically by a curved arrow, and the path is from the central controller's S2 node along the upper conductor to the satellite's S2 node, through the satellite's internal circuitry (the conduction path is shown as a dashed line), back from the satellite's S1 node along the lower conductor to the central controller's S1 node.

The middle and right portions of the figure show two pacing regimes. For the regime shown in the middle portion of the figure, the satellite is configured so that electrode 102b is connected to the upper conduction path and electrode 102c is connected to the lower conduction path. The current flow is shown schematically by a curved arrow, and the path is from the central controller's S2 node along the upper conductor to the satellite's S2 node, along a low-impedance path through the satellite's switches to electrode 100b, through the subject's body to electrode 100c, through an additional low-impedance path through the satellite's switches to the satellite's S1 node (the low-impedance conduction paths through the satellite are shown as solid lines), back from the satellite's S1 node along the lower conductor to the central controller's S1 node. Thus the pacing current is caused to flow through a small region of tissue between electrodes 102*b* path and 102*c*.

The right portion shows a regime where the central controller's S2 node is disconnected from the upper conductor, and connected to the outside of the controller (pacing can). As shown, the satellite is configured so that electrode 100*c* is connected to the lower conductor so the current flows from the central controller's S2 node to the outside of the can, through the subject's body to electrode 100*c*, through a low-impedance path through the satellite's switches to the satellite's S1 node (the low-impedance conduction path through the satellite is shown as a solid line), back from the satellite's S1 node along the lower conductor to the central controller's S1 node. In this regime, it would also be possible to have multiple electrodes connected to the lower conductor, although for a cylindrical electrode arrangement as shown in FIG. 3, the connections would likely be to no more than the two electrodes that are closest to the tissue to be stimulated.

One-Wire Embodiments

If other signals are not carried on bus conduction path S2, bus conduction path S2 may be eliminated and the subject's body fluids may be used as a power and data conductor. This is described in additional detail in the above referenced U.S. Provisional Patent Application No. 60/607,280, filed Sep. 2, 2004, titled "One Wire Medical Monitoring and Treating Devices."

For example, in the circuit described in FIG. 2, a single wire S1 connects central controller 10 with the S1 terminal on satellite units 20*a*, 20*b*, . . . . The satellite units' S2 terminals may be connected to an electrode on the satellite unit (electrode 105 FIG. 3) that contacts the body tissue. A conduction path is then established between the outer surface of the pacing can, the body tissue, the electrode, and S2. Coupled with S1, these two conduction paths form a loop through which power and data may data may be transmitted. Initially, this loop represents a relatively high impedance loop (100's of kilo-ohms) through which relatively low currents are able to flow. These currents are well below that required to stimulate tissue (for example 10's of micro-amps). In this state, these very low currents are used to transmit data to the satellite units where the data is stored.

This stored data is then used to control relatively very low impedance transistors between selected electrodes and S1. Once these switches are enabled, a relatively low impedance loop (100's of ohms) is established through which much higher levels of current are able to flow. It is these much high levels of current that are used to stimulate tissue near the selected electrodes. The selected electrodes through the enabled transistors are also used allow relatively low current and low potential (less than the threshold current of the switch transistor) signals to pass with low additional noise back to the central controller where they are compared to the potential on the surface of the can that houses the central controller (or other electrode), amplified and digitized for use by the rest of the system. It is one of the teachings of this invention that the enabled switches are able to maintain their function (either high impedance or very low impedance) while the conduction loop is not providing power to the satellite unit.

In the implementation with a fifth electrode 105 (see FIG. 3) connected to the satellite chip's S2 terminal, the current for programming the device flows in a loop described by: Drive electronics in can>S1 (the one-wire going down the lead) >Chip as Vss>Vdd>S2>electrode contacting the blood>Outer surface of the pacing can>Drive electronics.

As mentioned above, electrode 105 is optional. In an implementation where there is no fifth electrode, and S2 is only an internal node on the chip, no external connection is made to S2. In this embodiment, leakage current from one or more electrodes to internal node S2 is sufficient to charge up "vhigh" and also sufficient to send communication signals to the DCR. Once the signals are sent, the switches selectively connecting some—but not all—of the electrodes to S1 are set. Then, the pacing current can flow from the can, through the selected electrode, to S1, and back to the can. In the mode where the central controller is sending data, but not pacing, the chip presents a high-impedance path to current and signals are sent in this loop: Can>blood/tissue>Electrodes>S1 via diode-connected CMOS in EPAD>circuitry>S1>electronics in Can.

Once the switches are set, the chip creates a low impedance connection between one or more of the electrodes and S1 and the primary current loop becomes: Can>Blood/tissue>Electrodes>to S1 via set switch on chip>S1>can. When resetting the switch connections or clearing them, both current loops exist simultaneously. One "feature" of this embodiment is that not all four electrodes may be connected to S1—one must be left as a diode-connected CMOS switch for supplying "Vs2" to the circuit.

One-Wire Programming and Pacing

FIG. 16B is a schematic representation of programming and pacing with two one-wire embodiments of the invention. The left and middle portions of the figure show a central controller and a single satellite, designated 20' in that it differs from satellites 20*a* . . . 20*d* in FIG. 2 by virtue of having the optional fifth electrode 105. The central controller and the satellite have corresponding S1 and S2 terminals (nodes). The connection between the central controller's S1 node and the satellite's S1 node is through a bus conduction path having a dedicated conductor that is insulated from the subject's body. However, there is no dedicated conductor between the central controller's S2 node and the satellite's 82 node. Rather, the central controller's S2 node connected to the outside of the controller (pacing can) and the satellite's S2 node is connected to dedicated electrode 105, which contacts the subject's body. Thus the second conduction path includes and is in large part defined by the subject's body.

The left portion of FIG. 16B show-programming the satellite. This case is analogous to the case of programming the two-wire embodiment discussed in connection with the left portion of FIG. 16A except that the subject's body substitutes for the upper dedicated conductor. The middle portion of FIG. 16B show pacing, and this is exactly like the second example shown in the right portion of FIG. 16A.

The right portion of FIG. 16B shows the embodiment where there is no dedicated electrode for the second bus conduction path (S2). Rather, the satellite's S2 node is not associated with any particular electrode. Programming is accomplished by establishing a path between one of the electrodes, say electrode 100*a*, and the satellite's S2 node. Programming then proceeds, but it is not possible to specify any different state for electrode 100*a*.

Additional Embodiments (AC Signals, Hybrid Conduction Paths)

Figure 17:
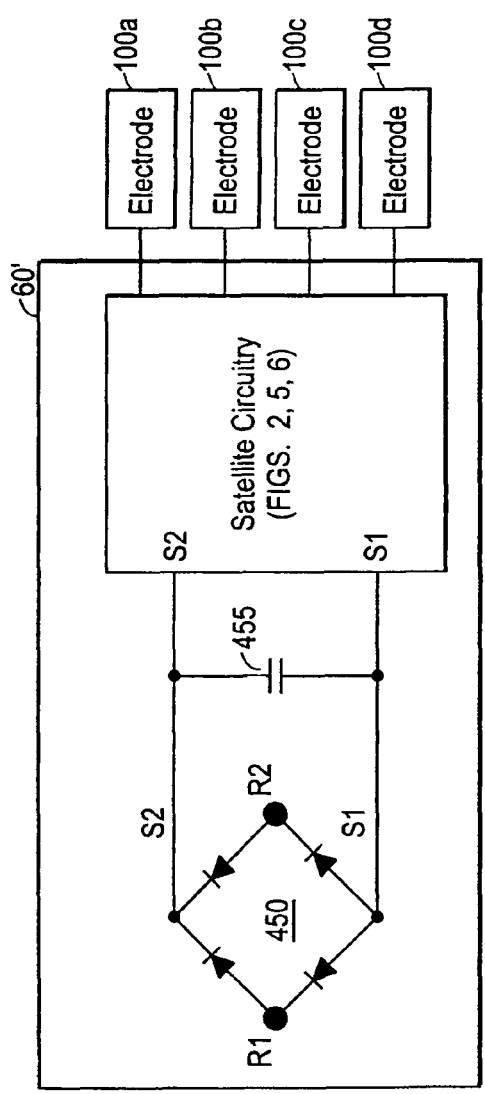
FIG. 17 is a block diagram of an embodiment of a satellite that receives AC voltages.

FIG. 17 of a block diagram of a satellite adapted from the previously described embodiments to receive and process AC signals over the bus. The satellite circuitry is denoted with the reference numeral 60' to signify that it corresponds to satellite circuitry 60 shown in FIGS. 2 and 5 (as well as the more detailed circuit schematics). In short, the satellite circuitry includes a rectifier 450, shown as a diode bridge, and a capacitor 455, which may not be needed. The satellite is shown as having two terminals, drawn as larger black dots, designated R1 and R2 that are coupled to the bus and provide the inputs to rectifier 450. The rectified output nodes are designated S1 and S2 with S2 being at the higher DC voltage. The rectified output signal can be applied to the remaining portions of the satellite circuitry, which may be substantially identical to the embodiments described in previous sections.

Figure 18:
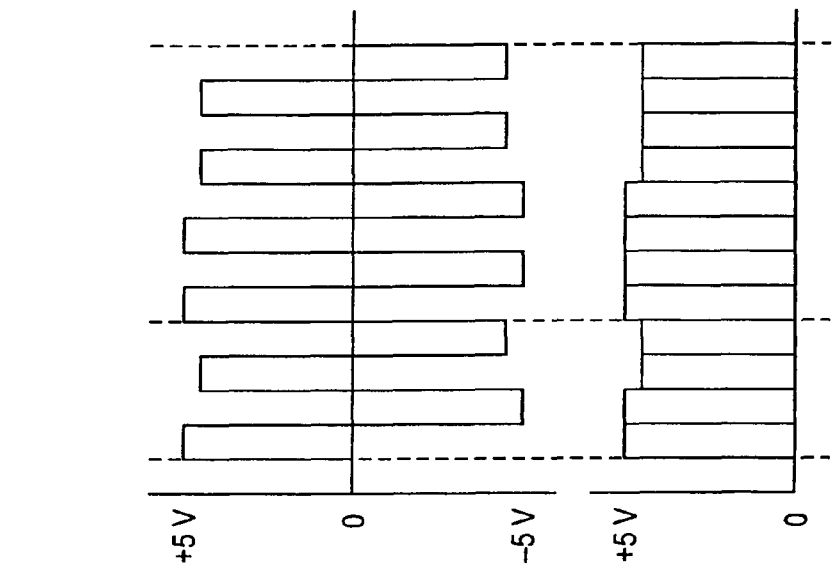
FIG. 18 is a timing diagram showing how to modulate the AC signal sent to the satellite.

FIG. 18 is a timing diagram showing how the AC signal may be configured so that, when rectified, it would generally match the modulated signal shown in FIG. 4. In the particular implementation, different bit values are represented by different periods for a square wave. Also, in the particular implementation, the modulation is between 4.5 volts and 5 volts. The timing diagram includes an upper portion showing the AC voltage, and a lower portion showing the rectified voltage. The particular example is a "0" bit followed by a "1" bit. As can be seen, the "0" bit is achieved by rectifying one cycle having an amplitude of 5 volts followed by one cycle having an amplitude of 4.5 volts. The "1" bit is achieved by rectifying two cycles having an amplitude of 5 volts followed by two cycles having an amplitude of 4.5 volts.

Figure 19:
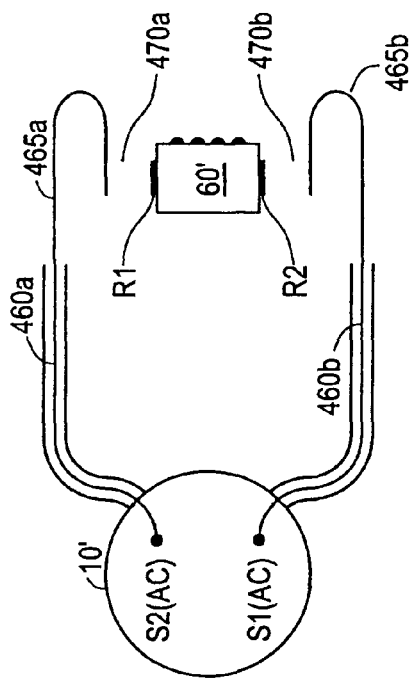
FIG. 19 is a block diagram showing the satellite of FIG. 17 in a system with hybrid bus conduction paths.

FIG. 19 shows satellite 60' incorporated into a system using hybrid conductive bus paths. The central controller is designated 10' signifying that it generally corresponds to previously described central controller 10. Each bus conduction path includes a first-portion 460 provided by an insulated conductor, a second portion 465 provided by a dedicated conductor and/or electrode and/or mesh (for example a defibrillation-type electrode) that is not insulated from the subject's body, and a third portion 470 that is provided by the subject's body fluids and/or tissue.

Thus, the current loop would begin at the controller electronics, through an insulated wire, through an uninsulated wire and/or electrode and/or mesh, through body tissue, through a wire or electrode, to the satellite's R2 input, through the satellite's circuitry, through the satellite's R1 input, through body fluids and/or tissue, through an uninsulated wire and/or electrode and/or mesh, through an insulated wire and back to the controller electronics.

The satellite is shown with electrodes R1 and R2 that contact the body at some distance apart, this distance in many ways defining the efficiency of power transmission. The satellite is also shown with four (for example) electrodes that are programmed to be connected to either of the satellite's S1 or S2 nodes (or disconnected from both). To program this satellite, the pacing can/controller would first place the programming code onto a high-frequency carrier signal (high enough that the signal cannot cause pacing at the broadcast voltage) and broadcast this signal between the two electrodes contacting the body fluid and/or tissue. The circuitry on the satellite would first rectify the AC signal into a DC signal. This signal would then go into circuitry substantially similar to that described above to control which electrodes would be connected or disconnected to S1 or S2.

An example of how this might be used clinically is for conductive path portion 465a to be or terminate in a defibrillation coil implanted in the right ventricle and conductive path portion 465b to be or terminate in a metal mesh implanted subcutaneously under the skin over the heart. The satellite might, for example, be mounted on a stent (producing a "satellite-stent") that is placed for therapeutic reasons into the coronary artery. The satellite would have two electrodes R1 and R2 that are some distance apart to pick up the AC signal from the defibrillation coil and the implanted mesh. The satellite would have two other electrodes that may be programmed to be connected to S1 and S2, forming a bipolar electrode pair. When they are programmed to be connected, a high frequency signal imposed between the defibrillation coil and the mesh will cause a DC voltage to appear across the bipolar electrodes. This DC voltage will "capture" the myocardial tissue. In operation, this "pacing-stent" may be first used to try to defibrillate the heart before using up a lot of power to defibrillate the customary way. Multiple pacing-stents might be used simultaneously for this purpose.

Another variation of the satellite-stent is as it is used with other types of effectors, such as pressure sensors that would determine if restenosis has partially occluded the "satellite-stent." The "active-stent" would then emit a code that is representative of the pressure through the electrodes that are connected to S1 and S2, perhaps using a different carrier frequency. This signal would then be picked up by a pair of nearby (which may be the same or nearby the same electrodes that broadcast the first AC signal).

AC embodiments such as this may improve the reliability of the "one-wire" and "two-wire" embodiments, as well, be reducing the corrosion that might appear between the two wires or the one-wire and the body.

Terminology

Some embodiments of the present invention provide multiplexed carrier devices and systems, and methods for configuring and using multiplexed carriers. By "multiplexed" or "multiplexing," it is generally meant that a carrier may carry two or more effectors which may transmit and/or receive signals to and/or from one or more "remote" devices. A remote device may be located anywhere, either on the carrier or apart from the carrier. Central controller 10 is, from the point of view of the satellite, a remote device.

Generally, multiplexing may be accomplished by any of a number of different techniques. One technique, for example, may be referred to generally as "broadcasting." A second multiplexing technique may be referred to as "frequency-domain multiplexing." A third exemplary multiplexing technique may be referred to as "time-domain multiplexing." Other multiplexing techniques involve addressing, whereby each effector has a digital address or number. Any of these techniques, or any other suitable techniques; may be used in a multiplexed carrier of the invention. In some embodiments, for example, combinations of the above described techniques may be used, such as a combination of frequency-domain and time-domain multiplexing.

The term "effectors" is generally used herein to refer to sensors, actuators, sensor/actuators, or any other device that may be coupled with a carrier for performing a function. In some embodiments, for example, the at least two identifiable effectors comprise a transducer and a processor (digital or analog), where the processor is identifiable and distinguishable from all other effector processors using conventional multiplexing circuitry.

The effectors may be intended for collecting data, such as but not limited to pressure data, volume data, dimension data, temperature data, oxygen or carbon dioxide concentration data, hematocrit data, electrical conductivity data, electrical potential data, pH data, chemical data, blood flow rate data, thermal conductivity data, optical property data, cross-sectional area data, viscosity data, radiation data and the like. Alternatively, the effectors may be intended for actuation or intervention, such as providing an electrical current or voltage, setting an electrical potential, heating a substance or area, inducing a pressure change, releasing or capturing a material or substance, emitting light, emitting sonic or ultrasound energy, emitting radiation and the like.

In some embodiments, both sensor(s) and actuator(s) may be coupled with a carrier. In one embodiment, at least some of the effectors include a transducer and an electronic conversion circuit, wherein output from the transducer is encoded using a carrier frequency and broadcast onto one of the electrical conductors, and wherein each effector utilizes a different carrier frequency. Alternatively, at least some of the effectors may include a transducer and an electronic conversion circuit, wherein output from the transducer is broadcast onto one of the electrical conductors during a specified time interval, and wherein each effector utilizes a different time interval.

The data collected may include any one of pressure data, volume data, dimension data, temperature data, oxygen or carbon dioxide concentration data, hematocrit data, electrical conductivity data, electrical potential data, pH data, chemical data, blood flow rate data, thermal conductivity data, optical property data, cross-sectional area data, viscosity data, radiation data and the like. Typical methods will be performed where the sensors are distributed and the catheter present in the vasculature and/or within a chamber of the heart. Other methods will be performed where the sensors are distributed on a flat surface and the surface is present on or near brain tissue. Still other methods will be performed where the sensors are distributed and the catheter present in the urinary tract, reproductive tract, endoscopic surgical site, abdominal cavity, gastrointestinal tract or a joint space.

The effectors may be mounted to a surface of the carrier or may be disposed within the body of the carrier. In various embodiments, such multiplexed carriers may be used for sensing any of a variety of data, such as pressure data, volume data, dimension data, temperature data, oxygen or carbon dioxide concentration data, hematocrit data, electrical conductivity data, electrical potential data, pH data, chemical data, blood flow rate data, thermal conductivity data, optical property data, cross-sectional area data, viscosity data, radiation data and the like.

Alternatively, the effectors may be intended for actuation or intervention, such as providing an electrical current or voltage, setting an electrical potential, heating a substance or area, inducing a pressure change, releasing or capturing a material, emitting light, emitting sonic or ultrasound energy, emitting radiation and/or the like. Carriers may also be used in a variety of locations within a body, such as in one or more chambers of the heart, in arterial or venous vasculature, in or on brain tissue, in the urinary, gastrointestinal or reproductive tracts, in the abdominal cavity, in a joint space or the like.

CONCLUSION

In conclusion, it can be seen that embodiments of the present invention may provide one or more of the advantages mentioned above or discussed below.

The exemplary control circuit described above allows several unique features and functions to be implemented in a cardiac pacing/signal detection system. One such feature is that the system can address and individually pace through the two bus conduction paths residing within a pacing lead. In addition, the system can collect unamplified analog signals through the satellite electrodes over the same two wires. This feature significantly reduces the complexity of the system and provides unprecedented flexibility which has not been available in conventional pacing systems.

Another advantage of the embodiments of the satellite circuitry is that, by using specifically designed digital logic, the system can provide power supply and facilitate digital communication simultaneously over the two bus conduction paths. Specifically, the satellite circuitry can extract a DC power supply derive a clock signal, and capture the modulated bit sequences at the same time. Furthermore, the special initialization generation circuit ensures that during a power-up period, each satellite is not misconfigured by accident.

In addition, embodiments of the satellite circuitry can result in an extremely low power consumption. This is because the unique functions of the satellite circuitry are implemented with special device-level designs to minimize leakage current. For example, exemplary satellite circuitry may adopt specific CMOS designs with long gate lengths to reduce the amount of leakage current through the gates. Additionally, embodiments of the satellite circuitry may have extra substrate contacts and vias. Because of these low-leakage-current design features, a significant portion of the control circuit can be turned off between two consecutive recharges while the circuit remains in a configured state.

While the above is a complete description of specific embodiments of the invention, the above description should not be taken as limiting the scope of the invention as defined by the claims.

What is claimed is:

1. An implantable integrated circuit to control an electrode, the implantable integrated circuit comprising:
   a power recovery circuit configured to supply power;
   a data/clock recovery circuit configured to derive and recover digital data signal to control the electrode, wherein the data/clock recovery circuit is further configured to implement a sleep state of the data/clock recovery circuit in response to a receipt of a sleep signal;
   a command interpretation circuit configured to receive the digital data signal from the data/clock recovery circuit and to map the digital data signals into control commands; and
   an electrode control circuit configured to receive the control commands from the command interpretation circuit and to identify and control the electrode based on the control commands.

2. The implantable integrated circuit according to claim 1, wherein the power recovery circuit comprises a capacitor.

3. The implantable integrated circuit according to claim 1, further comprising an initialization generation circuit configured to generate initialization signals when the digital data signals exceed predetermined voltage thresholds.

4. The implantable integrated circuit according to claim 1, wherein the electrode control circuit comprises electrode registers.

5. The implantable integrated circuit according to claim 1, wherein the electrode control circuit comprises electrode drivers and switches.

6. The implantable integrated circuit according to claim 1, wherein the power recovery circuit is refreshed by drawing a current of a few picoamps.

7. The implantable integrated circuit according to claim 1, further comprising a bus.

8. The implantable integrated circuit according to claim 7, wherein the bus is a two-wire bus.

9. The implantable integrated circuit according to claim 7, wherein the electrode control circuit is coupled to one or more electrodes in addition to the electrode.

10. The implantable integrated circuit according to claim 1, wherein the data/clock recovery circuit is coupled to a central controller of the electrode.

11. The implantable integrated circuit according to claim 10, wherein the central controller comprises a pacemaker.

12. The implantable integrated circuit according to claim 10, wherein the central controller comprises a switching circuit.

* * * * *